United States Patent [19]

Meinke et al.

[11] Patent Number: 5,208,222

[45] Date of Patent: May 4, 1993

[54] 4''-AND 4'-ALKYLTHIO AVERMECTIN DERIVATIVES

[75] Inventors: Peter T. Meinke, New York, N.Y.; Helmut Mrozik, Matawan, N.J.

[73] Assignee: Merck & Co., Inc., Rahway, N.J.

[21] Appl. No.: 676,626

[22] Filed: Mar. 28, 1991

[51] Int. Cl.$^5$ ................. A61K 31/70; A61K 31/365
[52] U.S. Cl. ................................. 514/30; 514/210; 514/320; 514/321; 514/337; 514/338; 514/422; 514/430; 514/432; 514/444; 514/450; 548/525; 548/526; 548/950; 548/962; 546/196; 546/197; 546/269; 546/270; 549/13; 549/60; 549/88; 549/90; 536/7.1
[58] Field of Search .......... 514/824, 450, 30; 549/264; 536/7.1

[56] References Cited

U.S. PATENT DOCUMENTS

| | | | |
|---|---|---|---|
| 3,950,360 | 4/1976 | Aoki et al. | 549/264 |
| 4,171,314 | 10/1979 | Chobale et al. | 549/264 |
| 4,173,571 | 11/1979 | Chibala et al. | 549/264 |
| 4,199,569 | 4/1980 | Chabala et al. | 514/30 |
| 4,201,861 | 5/1980 | Mrozik et al. | 536/7.1 |
| 4,206,205 | 6/1980 | Mrozik et al. | 514/30 |
| 4,289,760 | 9/1981 | Mrozik et al. | 549/264 |
| 4,310,519 | 1/1982 | Albers-Schonberg et al. | 514/30 |
| 4,427,663 | 1/1984 | Mrozik | 536/7.1 |
| 4,622,313 | 11/1986 | Wyvratt, Jr. | 514/30 |
| 4,696,945 | 9/1987 | Frei et al. | 514/450 |
| 4,806,527 | 2/1989 | Christensen et al. | 549/264 |
| 4,849,446 | 7/1989 | Asato et al. | 549/264 |
| 4,859,657 | 8/1989 | O'Sullivan et al. | 514/63 |
| 4,873,224 | 10/1989 | Linn et al. | 514/30 |
| 4,897,416 | 1/1990 | Frei et al. | 514/450 |
| 4,906,619 | 3/1990 | Eskola et al. | 536/7.1 |
| 4,916,120 | 4/1990 | Roben et al. | 536/7.1 |

FOREIGN PATENT DOCUMENTS

| | | |
|---|---|---|
| 4752785 | 3/1986 | Australia . |
| 0170006A2 | 2/1986 | European Pat. Off. . |
| 0214731A2 | 3/1987 | European Pat. Off. . |
| 0276131A2 | 7/1988 | European Pat. Off. . |
| 0340849 | 11/1989 | European Pat. Off. . |
| 0340849A2 | 11/1989 | European Pat. Off. . |
| 0430884A1 | 11/1990 | European Pat. Off. . |
| 0045281 | 2/1988 | Japan . |
| 2166436A | 5/1986 | United Kingdom . |

OTHER PUBLICATIONS

Chen et al. (I) *Abst. Pap. Am. Chem. Soc.* 186 p. MBTD 28, 1983.

T. Chen et al., (II) *Arch. Biochem. Biophys.* 269, pp. 544–547 1989.

M. D. Schulman et al., *The Journal of Antibiotics*, 38, 1494–1498 1985.

M. D. Schulman et al., (II) *Antimicrobial Agents and Chemotherapy* 31, pp. 744–747 (1987).

Fisher et al., *Macrolide Antibiotics*, Omura (Ed), Academic Press: New York 553–606 (1984).

Davies et al., *Nat. Prod. Rep.* 3, 87–121 (1986).

Shih et al. (I) *Tet. Lett.* 31, 3525–28 (1990).

Shih et al. (II) *Tet. Lett.* 31, 3529–3532 (1990).

*Primary Examiner*—C. Warren Ivy
*Assistant Examiner*—A. A. Owens
*Attorney, Agent, or Firm*—David L. Rose; Joseph F. DiPrima; Catherine A. Dolan

[57] ABSTRACT

Avermectin derivatives are disclosed wherein the 4''-hydroxy group is replaced by a substituted alkylthio or acylthio group or an iodo group. These avermectin derivatives can be further derivatized at the 5- and 23-positions as ketoximes or O-substituted ketoximes. The 4''-substituted avermectin derivatives are prepared from the 4''- and 4'-trifluoromethanesulfonyl avermectin derivatives with halo- or sulfur-containing nucleophiles. The 4''- and 4'-α- and β-trifluoromethane sulfonates are prepared selectively and converted into 4''- or 4'-alkyl- or acylsulfides, or iodides using the appropriate sulfur-containing or iodine nucleophile. Substituted sulfoxy and sulfonyl substituents at the 4''- and 4'-positions are prepared from oxidation of the corresponding substituted sulfides. The new compounds are potent antiparasitic agents; in particular, the compounds are anthelmintic, insecticidal and acaricidal agents.

8 Claims, No Drawings

4''- AND 4'-ALKYLTHIO AVERMECTIN DERIVATIVES

BACKGROUND OF THE INVENTION

The term avermectin (previously referred to as C-076) is used to describe a series of compounds isolated from the fermentation broth of an avermectin-producing strain of Streptomyces avermitilis and derivatives thereof. The morphological characteristics of the culture are completely described in U.S. Pat. No. 4,310,519. The avermectin compounds are a series of macrolides, each of which is substituted at the 13 position with a 4-(α-L-oleandrosyl)-α-L-oleandrose group. The avermectin compounds and the derivatives of this invention have a very high degree of anthelmintic and anti-parasitic activity.

The avermectin series of compounds isolated from the fermentation broth have the following structure:

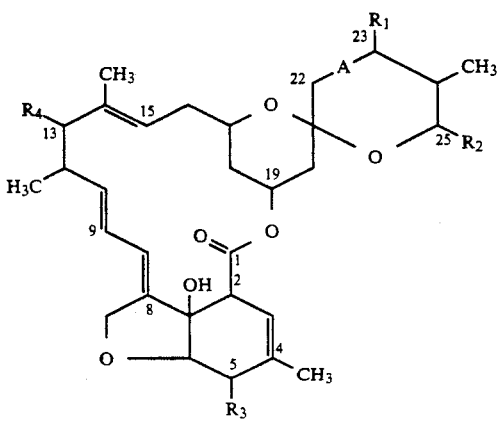

wherein

R₄ is the 4'α-(L-oleandrosyl)-α-L-oleandrosyloxy group of the structure

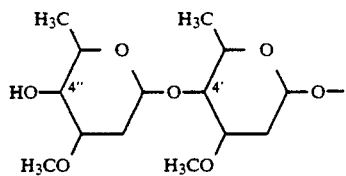

and wherein

A at the 22,23 position indicates a single or a double bond;

$R_1$ is a hydrogen or hydroxy and is hydroxy only when A indicates a single bond;

$R_2$ is iso-propyl or sec-butyl; and $R_3$ is methoxy or hydroxy.

There are eight different avermectin natural product compounds and they are given the designations A1a, A1b, A2a, A2b, B1a, B1b, B2a, and B2b based upon the structure of the individual compounds. In the foregoing structural formula, the individual avermectin compounds are as set forth below.

| (The R group is 4'-α-(L-oleandrosyl)-α-L-oleandrosyloxy.) | | | |
|---|---|---|---|
| | (A) | $R_1$ | $R_2$ | $R_3$ |
| A1a | double bond | — | sec-butyl | —OCH₃ |
| A1b | double bond | — | iso-propyl | —OCH₃ |
| A2a | single bond | —OH | sec-butyl | —OCH₃ |
| A2b | single bond | —OH | iso-propyl | —OCH₃ |
| B1a | double bond | — | sec-butyl | —OH |
| B1b | double bond | — | iso-propyl | —OH |
| B2a | single bond | —OH | sec-butyl | —OH |
| B2b | single bond | —OH | iso-propyl | —OH |

The avermectin compounds are generally isolated as mixtures of a and b components. Such compounds differ only in the nature of the $R_2$ substituent and the minor structural differences have been found to have very little effect on the isolation procedures, chemical reactivity and biological activity of such compounds.

In addition to these natural avermectins containing the 25-iso-propyl or 25-sec-butyl-substituent, closely related derivatives containing other branched or cyclic 25-alkyl or 25-alkenyl substituents, including those further substituted by heteroatoms such as oxygen, sulfur, nitrogen, and halogen, are known in the literature. These derivatives are obtained through various adjustments and additions to the fermentation procedures as described fully in the European Patent Application EPO 0 214 731.

Avermectins are products of microbial fermentations using the actinomycete Streptomyces avermitilis. These microbes use acetates and propionates as building blocks for most of the avermectin carbon chain, which is then further modified by microbial enzymes to give the completed avermectin molecules. It is known, however, that the carbon C-25 and the 2-propyl and 2-butyl substituents at this carbon are not derived from acetate or propionate units, but are derived from the amino acids L-valine and L-isoleucine, respectively. These acids then have been found to be directly incorporated into the avermectin structures to give the 2-propyl and 2-butyl C-25 substituents, as is reported by Chen et al., Abstr. Pap. Am. Chem. Soc. (186 Meet., MBTD 28, 1983). It was also disclosed in European Patent Application number 0 214 731 that additions of large amounts of other acids such as cyclopentanoic, cyclobutyric, 2-methylpentanoic, 2-methylhexanoic, thiophene-3-carboxylic acids and others to the fermentation broth of S. avermitilis causes the microbes to accept these acids as substitutes and to make small amounts of avermectins containing these acids in form of new C-25 substituents. Examples of such new avermectin derivatives are:

25-(thien-3-yl)-25-des-(2-butyl)-avermectin A2a
25-(cyclohex-3-enyl)-25-des-(2-butyl)-avermectin A2a
25-cyclohexyl-25-des-(2-butyl)-avermectin A2a
25-(1-methylthioethyl)-25-des-(2-butyl)-avermectin A2a
25-(2-methylcyclopropyl)-25-des-(2-butyl)-avermectin A2a Similar experiments producing avermectins "c" and "d" containing as C-25 substituents a 2-pentyl and 2-hexyl group are described by T. S. Chen, et al. in Arch. Biochem. Biophys. 1989, 269, 544–547.

Still additional avermectin derivatives are produced through artificial modification of the fermentation of Streptomyces avermitilis either by addition of metabolic inhibitors such as sinefungin (as described by Schulman et al., J. Antibiot. 1985, 38, 1494–1498) or by mutation of the parent strain (as described by Schulman et al., Antimicrobial *Agents and Chemotherapy*, 1987, 31, 744–747, and by EP-276-131-A to Pfizer Inc.). Some of these avermectin derivatives are still further modified and are missing one or two of the 3'- and 3"-O-methyl groups (Schulman et al., *J. Antibiot.* 1985, 38, 1494–1498). Examples of such derivatives are:

3',3"-Bisdesmethyl-avermectin B1a and B1b
3',3"-Bisdesmethyl-avermectin B2a and B2b
3"-Desmethyl-avermectin B1a and B1b
3"-Desmethyl-avermectin B2a and B2b
3',3"-Bisdesmethyl-25-cyclohexyl-25-des-(2-butyl)-avermectin B2a
3',3"-Bisdesmethyl-25-cyclopentyl-25-des-(2-butyl)-avermectin B2a
3',3"-Bisdesmethyl-25-(3-thienyl)-25-des-(2-butyl)-avermectin B2a
3',3"-Bisdesmethyl-25-(3-furyl)-25-des-(2-butyl)-avermectin B2a
3',3"-Bisdesmethyl-25-(1-methylthioethyl)-25-des-(2-butyl)-avermectin B1a.

The fermentation products have been chemically modified in order to obtain further antiparasitic and insecticidal analogs with improved properties. Publications of such procedures in the scientific and patent literature have been reviewed by Fisher, M. H.; Mrozik, H.; in *Macrolide Antibiotics*; Omura, S., Ed.; Academic: New York, 1984; pp. 553–606, and by Davies, H. G.; Green, R. H. *Nat. Prod. Rep.*, 1986, 3, 87–121.

For example, a group of semisynthetic avermectin derivatives were obtained by hydrogenating specifically the 22,23-double bond of avermectin B1 giving 22,23-dihydroavermectin B1 derivatives which have very potent anthelmintic and antiparasitic properties. Other examples of semisynthetic avermectin derivatives contain a 8,9-oxide group, a 4-α-hydroxy or acyloxy group, a 23-keto group, which all are potent antiparasitic and insecticidal compounds.

These compounds may be used as starting materials for the compounds of this invention without further modification, or when containing additional reactive groups, which are not to be modified under the reaction conditions applied, only after protection of such with a suitable protecting group.

SUMMARY OF THE INVENTION

The present invention is concerned with derivatives of avermectin compounds wherein the 4'-or 4"-hydroxy group is replaced by a substituted alkyl- or acylthio group or an iodo group. The iodo-group is a good leaving group and can be replaced by other nucleophiles. The substituted alkyl- or acylthio analogs may also be further modified. Thus it is the object of this invention to describe such compounds. It is a further object of this invention to describe the processes useful for the preparation of such compounds and intermediates prepared in the process. A still further object is to describe the use of such compounds as anthelmintic, insecticidal, and acaricidal agents. Still further objects will become apparent from the reading of the following description.

DESCRIPTION OF THE INVENTION

The compounds of the present invention have the following structural formula:

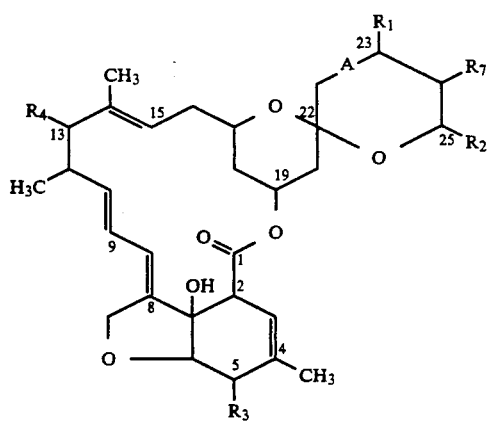

wherein:
A at the 22,23 position represents
(1) a single bond and wherein $R_1$ is
(a) hydrogen,
(b) hydroxy, or
(c) oxo; or
(2) a double bond and $R_1$ is absent;
$R_2$ is
(1) $C_{1-4}$ alkyl,
(2) substituted $C_{1-4}$ alkyl with 1 to 3 substituents selected from $C_{4-6}$ cycloalkyl, phenyl, and halo, especially fluoro,
(3) alpha-branched $C_{3-8}$ alkyl, especially isopropyl or sec-butyl,
(4) $C_{2-8}$ alkenyl, especially an alpha-branched $C_{3-8}$ alkenyl group,
(5) $C_{2-6}$ alkynyl,
(6) $C_{1-6}$ alkoxy $C_{1-6}$ alkyl,
(7) $C_{1-6}$ alkylthio $C_{1-6}$ alkyl,
(8) $C_{4-6}$ cycloalkyl or $C_{4-6}$ cycloalkenyl either unsubstituted or substituted with 1 to 3 substituents selected from
(a) methylene,
(b) halo, especially fluoro, and
(c) $C_{1-4}$ alkyl, or
(9) 3 to 6 membered nitrogen, oxygen or sulfur containing heterocycle, saturated or unsaturated, either unsubstituted or substituted with 1 to 3 substituents selected from
(a) $C_{1-4}$ alkyl, and
(b) halo, or
(10) phenyl, either substituted or unsubstituted with 1 to 3 substituents selected from
(a) $C_{1-3}$ alkyl, and
(b) halo, especially fluoro;
$R_3$ is
(1) hydroxy,
(2) $C_{1-6}$ alkoxy,
(3) $C_{2-6}$ alkanoyloxy,
(4) oxo, or
(5) oximino;
$R_7$ is hydrogen or $C_{1-6}$ alkyl, either straight chain or branched; and
$R_4$ is

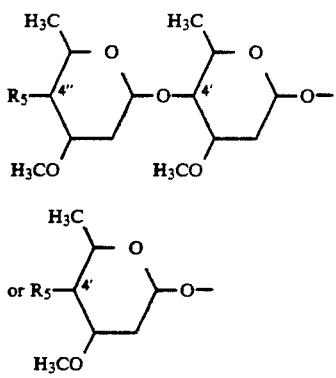

wherein:
R$_5$ is
- (1) S(O)$_n$R$_6$ wherein n is 0, 1 or 2,
- (2) SCOR$_6$, or
- (3) iodo;

wherein:
R$_6$ is
- (1) hydrogen,
- (2) C$_{1-8}$ alkyl either straight or branched chain and either unsubstituted or substituted with 1-3 substitutents selected from
  - (a) halo,
  - (b) hydroxy,
  - (c) C$_{1-3}$ alkoxy,
  - (d) phenoxy,
  - (e) C$_{1-3}$ alkylthio,
  - (f) C$_{1-3}$ alkylsulfinyl,
  - (g) C$_{1-3}$ alkylsulfonyl,
  - (h) amino,
  - (i) C$_{2-6}$ alkanoylamino,
  - (j) C$_{1-3}$ alkylamino,
  - (k) di(C$_{1-3}$ alkyl)amino,
  - (l) halo C$_{1-3}$ alkoxycarbonylamino,
  - (m) oxo,
  - (n) carboxy, and
  - (o) C$_{1-3}$ alkoxycarbonyl,
- (3) C$_{2-8}$ alkanoyl either unsubstituted or substituted with 1-3 substitutents selected from
  - (a) halo,
  - (b) hydroxy,
  - (c) C$_{1-3}$ alkoxy,
  - (d) phenoxy,
  - (e) C$_{1-3}$ alkylthio,
  - (f) C$_{1-3}$ alkylsulfinyl,
  - (g) C$_{1-3}$ alkylsulfonyl,
  - (h) amino,
  - (i) C$_{2-6}$ alkanoylamino,
  - (j) C$_{1-3}$ alkylamino,
  - (k) di(C$_{1-3}$ alkyl)amino,
  - (l) halo C$_{1-3}$ alkoxycarbonylamino,
  - (m) oxo,
  - (n) carboxy, and
  - (o) C$_{1-3}$ alkoxycarbonyl,
- (4) C$_{3-8}$ cycloalkyl, either unsubstituted or substituted with 1-3 substitutents selected from
  - (a) halo,
  - (b) C$_{1-3}$ alkoxy,
  - (c) sulfonamido,
  - (d) amino,
  - (e) C$_{1-3}$ alkylamino,
  - (f) di(C$_{1-3}$ alkyl)amino, and
  - (g) C$_{2-6}$ alkanoylamino, or
- (5) nicotinoyl.

Preferred compounds of this invention are realized in the foregoing structural formula wherein
A at the 22,23 position represents a single bond and wherein R$_1$ is hydrogen or hydroxy, or A represents a double bond and R$_1$ is absent;
R$_2$ is an alpha-branched C$_3$–C$_8$ alkyl group, an alpha-branched C$_3$–C$_8$ alkenyl group, C$_{4-6}$ cycloalkyl, C$_{4-6}$ cycloalkenyl, phenyl, or p-fluoro-phenyl;
R$_3$ is hydroxy or oxime;
R$_7$ is methyl;
R$_4$ is

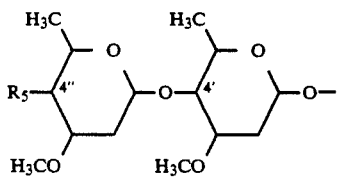

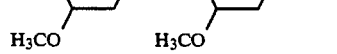

where
R$_5$ is
- (1) S(O)$_n$R$_6$ wherein n is 0, 1 or 2, or
- (2) SCOR$_6$;

wherein:
R$_6$ is
- (1) hydrogen,
- (2) C$_{1-4}$ alkyl either straight or branched chain and either unsubstituted or substituted with 1-3 substitutents selected from
  - (a) halo,
  - (b) hydroxy,
  - (c) C$_{1-3}$ alkoxy,
  - (d) C$_{1-3}$ alkylthio,
  - (e) C$_{1-3}$ alkylsulfonyl,
  - (f) amino,
  - (g) C$_{2-3}$ alkanoylamino,
  - (h) C$_{1-3}$ alkylamino,
  - (i) di(C$_{1-3}$ alkyl)amino,
  - (j) carboxy, and
  - (k) C$_{1-3}$ alkoxycarbonyl, or
- (3) C$_{2-5}$ alkanoyl either unsubstituted or substituted with 1-3 substitutents selected from
  - (a) halo,
  - (b) hydroxy,
  - (c) C$_{1-3}$ alkoxy,
  - (d) C$_{1-3}$ alkylthio,
  - (e) C$_{1-3}$ alkylsulfinyl,
  - (f) C$_{1-3}$ alkylsulfonyl,
  - (g) amino,
  - (h) C$_{1-3}$ alkanoylamino, and
  - (i) di(C$_{1-3}$ alkyl)amino.

The most preferred compounds are realized in the foregoing structural formula wherein
A at the 22,23 position represents a single bond and wherein R$_1$ is hydrogen or hydroxy, or A represents a double bond and R$_1$ is absent;
R$_2$ is 2-propyl, 2-butyl, 2-buten-2-yl, 2-penten-2-yl, 4-methyl-2-penten-2-yl, cyclohexyl, cyclohexenyl, cyclopentyl, cyclopentenyl, phenyl, or p-fluoro-phenyl;
R$_3$ is hydroxy;
R$_7$ is methyl; and
R$_4$ is

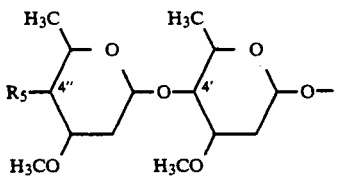

wherein
$R_5$ is $SCOR_6$ or $S(O)_nR_6$ wherein n is 0, 1 or 2; wherein:
$R_6$ is $C_{1-3}$ alkyl either straight or branched chain and either unsubstituted or substituted with 1-3 substituents selected from
(1) hydroxy,
(2) $C_{1-2}$ alkoxy,
(3) amino,
(4) acetylamino,
(5) $C_{1-2}$ alkylamino, and
(6) dimethylamino.
(7) halo Preferred compounds of this invention are further realized in the following compounds:

4″-deoxy-4″-epi-methylthio-avermectin B1a/B1b,
4″-deoxy-22,23-dihydro-4″-epi-methylthio-avermectin B1a/B1b,
4″-deoxy-4″-epi-methylsulfinyl-avermectin B1a/B1b,
4″-deoxy-4″-epi-methylsulfonyl-avermectin B1a/B1b,
4″-deoxy-4″-methylthio-avermectin B1a/B1b,
4″-deoxy-22,23-dihydro-4″-methylthio-avermectin B1a/B1b,
4″-deoxy-4″-methylsulfinyl-avermectin B1a/B1b,
4″-deoxy-4″-methylsulfonyl-avermectin B1a/B1b,
4″-deoxy-5-oximino-4″-epi-methylthio-avermectin B1a/B1b,
4″-deoxy-22,23-dihydro-5-oximino-4″-epi-methylthio-avermectin B1a/B1b,
4″-deoxy-5-oximino-4″-epi-methylsulfinyl-avermectin B1a/B1b,
4″-deoxy-5-oximino-4″-epi-methylsulfonyl-avermectin B1a/B1b,
4″-deoxy-5-oximino-4″-methylthio-avermectin B1a/B1b,
4″-deoxy-22,23-dihydro-5-oximino-4″-methylthio-avermectin B1a/B1b,
4″-deoxy-22,23-dihydro-5-oximino-4″-methylthio-avermectin B1a/B1b,
4″-deoxy-5-oximino-4″-methylsulfonyl-avermectin B1a/B1b,
4″-deoxy-4″-epi-octylthio-avermectin B1a/B1b,
4″-deoxy-4″-octylthio-avermectin B1a/B1b,
4″-deoxy-5-oximino-4″-octylthio-avermectin B1a/B1b,
4″-deoxy-5-oximino-4″-epi-octylthio-avermectin B1a/B1b,
4″-deoxy-22,23-dihydro-5-oximino-4″-octylthio-avermectin B1a/B1b,
4″-deoxy-22,23-dihydro-5-oximino-4″-epi-octylthio-avermectin B1a/B1b,
4″-deoxy-22,23-dihydro-4″-octylthio-avermectin B1a/B1b,
4″-deoxy-22,23-dihydro-4″-epi-octylthio-avermectin B1a/B1b,
4″-deoxy-4″-(2-hydroxyethyl)thio-avermectin B1a/B1b,
4″-deoxy-4″-epi-(2-hydroxyethyl)thio-avermectin B1a/B1b,
4″-deoxy-5-oximino-4″-(2-hydroxyethyl)thio-avermectin B1a/B1b,
4″-deoxy-5-oximino-4″-epi-(2-hydroxyethyl)thio-avermectin B1a/B1b,
4″-deoxy-22,23-dihydro-4″-(2-hydroxyethyl)thio-avermectin B1a/B1b,
4″-deoxy-22,23-dihydro-5-oximino-4″-(2-hydroxyethyl)thio-avermectin B1a/B1b,
4″-deoxy-22,23-dihydro-5-oximino-4″-epi-(2-hydroxyethyl)thio-avermectin B1a/B1b,
4″-deoxy-4″-(2-hydroxyethyl)sulfinyl-avermectin B1a/B1b,
4″-deoxy-4″-epi-(2-hydroxyethyl)sulfinyl-avermectin B1a/B1b,
4″-deoxy-5-oximino-4″-(2-hydroxyethyl)sulfinyl-avermectin B1a/B1b,
4″-deoxy-5-oximino-4″-epi-(2-hydroxyethyl)sulfinyl-avermectin B1a/B1b,
4″-deoxy-22,23-dihydro-4″-(2-hydroxyethyl)sulfinyl-avermectin B1a/B1b,
4″-deoxy-22,23-dihydro-4″-epi-(2-hydroxyethyl)sulfinyl-avermectin B1a/B1b,
4″-deoxy-22,23-dihydro-5-oximino-4″-(2-hydroxyethyl)sulfinyl-avermectin B1a/B1b,
4″-deoxy-22,23-dihydro-5-oximino-4″-epi-(2-hydroxyethyl)sulfinyl-avermectin B1a/B1b,
4″-deoxy-4″-(2-hydroxyethyl)sulfonyl-avermectin B1a/B1b,
4″-deoxy-4″-epi-(2-hydroxyethyl)sulfonyl-avermectin B1a/B1b,
4″-deoxy-5-oximino-4″-(2-hydroxyethyl)sulfonyl-avermectin B1a/B1b,
4″-deoxy-5-oximino-4″-epi-(2-hydroxyethyl)sulfonyl-avermectin B1a/B1b,
4″-deoxy-22,23-dihydro-4″-(2-hydroxyethyl)sulfonyl-avermectin B1a/B1b,
4″-deoxy-22,23-dihydro-4″-epi-(2-hydroxyethyl)sulfonyl-avermectin B1a/B1b,
4″-deoxy-22,23-dihydro-5-oximino-4″-(2-hydroxyethyl)-sulfonyl-avermectin B1a/B1b,
4″-deoxy-22,23-dihydro-5-oximino-4″-epi-(2-hydroxyethyl)-sulfonyl-avermectin B1a/B1b,
4″-deoxy-4″-epi-thioacetyl-avermectin B1a/B1b,
4″-deoxy-4″-thioacetyl-avermectin B1a/B1b,
4″-deoxy-5-oximino-4″-thioacetyl-avermectin B1a/B1b,
4″-deoxy-5-oximino-4″-epi-thioacetyl-avermectin B1a/B1b,
4″-deoxy-22,23-dihydro-5-oximino-4″-thioacetyl-avermectin B1a/B1b,
4″-deoxy-22,23-dihydro-5-oximino-4″-epi-thioacetyl-avermectin B1a/B1b,
4″-deoxy-22,23-dihydro-4″-thioacetyl-avermectin B1a/B1b,
4″-deoxy-22,23-dihydro-4″-epi-thioacetyl-avermectin B1a/B1b,
4″-deoxy-5-oximino-4″-epi-thiocyanato-avermectin B1a/B1b,
4″-deoxy-5-oximino-4″-epi-thiocyanato-avermectin B1a/B1b,
4″-deoxy-22,23-dihydro-5-oximino-4″-thiocyanato-avermectin B1a/B1b,
4″-deoxy-22,23-dihydro-5-oximino-4″-epi-thiocyanato-avermectin B1a/B1b,
4″-deoxy-22,23-dihydro-4″-thiocyanato-avermectin B1a/B1b,
4″-deoxy-22,23-dihydro-4″-epi-thiocyanato-avermectin B1a/B1b, 4'''-deoxy-4'''-epi-methylthio-25-des-(2-butyl)-25-cyclohexyl-avermectin, 4'''-deoxy-4'''-epi-methylthio-25-des-(2-butyl)-25-phenyl-avermectin, 4'''-deoxy-4'''-epi-methylthio-25-des-(2-butyl)-25-[2-(4-methylpenten-2-yl)]-avermectin, 4'''-deoxy-4'''-epi-(2-amino)ethylthio-25-des-(2-butyl)-25-cyclohexen-2-yl-avermectin, 4'''-deoxy-4'''-epi-trifluoromethylthio-avermectin B1a/B1b, 4'''-deoxy-4'''-epi-2,2,2-trifluoroethylthio-avermectin B1a/B1b, and 25-cylopentyl-25-des-(2-butyl)-4'''-epi-thioacetyl-avermectin B1a.

The monosaccharide analog of each of these compounds is included within the scope this invention.

In the present invention the term "loweralkyl" is intended to indicate those alkyl groups of from 1 to 6 carbon atoms such as methyl, ethyl, propyl, isopropyl, butyl, pentyl, hexyl, and the like, either straight or branched chain.

The term "loweralkoxy" is intended to include those alkoxy groups of from 1 to 8 carbon atoms such as methoxy, ethoxy, propoxy, isopropoxy, butoxy, pentoxy, hexoxy, heptoxy, octoxy, and the like, either straight or branched chain.

The term "loweralkanoyl" is intended to include those alkanoyl groups of from 1 to 6 carbon atoms such as formyl, acetyl, propionyl, buytryl, pentanoxyl, hexanoyl, and the like.

The terms "halo" and "halogen" are intended to include the halogen atoms: fluorine, chlorine, bromine, or iodine.

The above structural formula is shown without a definitive stereochemistry. However, during the course of the synthetic procedures used to prepare such compounds, the products of such procedures can be a mixture of stereoisomers. In particular, the stereoisomers at the 4''-, 4'-, 13-and 23-positions may be oriented either α- or β-representing such groups being below or above the general plane of the molecule, respectively. In each such case both the α- and β-configurations are intended to be included within the ambit of this invention. In certain cases the term "epi" is used to distinguish the stereoisomer being of opposite configuration to the natural compound at one specific asymmetrical carbon atom.

PREPARATION OF STARTING MATERIALS

The ultimate starting materials for the compounds of this invention are the avermectin fermentation products defined above. In addition, other microbially produced avermectin derivatives containing an alpha-branched alkyl or alkenyl group substituent at the 25-position designated in the structural formula as $R_2$ have been described in European patent application number 86305604.0 (publication number 0 214 731), 88300426.9 (0 276 131), and 88300354.3 (0 276 103). These compounds can also be used as starting materials for the compounds claimed in this invention. The $R_2$ substituent is inert under the reaction conditions employed for the preparation of the compounds of this invention, so that these reactions can also be carried out with these altered avermectin derivatives.

It is apparent that additional reactions are required to prepare the starting materials for the compounds of this invention. Specifically, reactions are carried out at the 4'', 4', 5, 22, 23, 24 and 25-positions. It is generally preferred to prepare whatever substituents are required at the 22, and 23 positions before conversion to a good leaving group at the 4''or 4'position and subsequent nucleophilic substitution of the leaving group with the thio-containing or iodo nucleophile. Such a reaction sequence generally avoids undesirable side reactions. This technique is not required, however, and if desired other sequences may be used.

In addition, during the oxidation and certain substitution reactions described above, it is necessary to protect the 5-hydroxy group to avoid substitution or oxidation at that position. With this position protected, the reactions may be carried out at the 4'''-or 4'-positions without affecting the remainder of the molecule. Subsequent to any of the above-described reactions, the protecting group may be removed and the unprotected product isolated. For compounds of this invention, conversion of the 5-hydroxy group to a ketone or ketoxime is preferably performed after substitution at the 4''- or 4'-position. The protecting group employed at the 5-position is ideally one which may be readily synthesized, will not be affected by the reactions at the 4''- and 4'-positions and may be removed without affecting any other functionality of the molecule. One preferred type of protecting group for the avermectin type of molecule is the tri-substituted silyl group, preferably the tri-loweralkyl silyl group. One especially preferred example is the tert.-butyldimethylsilyl group. The reaction preparing the protected compound is carried out by reacting the hydroxy compound with the appropriately substituted silylhalide, preferably the silylchloride in an aprotic polar solvent such as methylene chloride, benzene, toluene, ethyl acetate, tetrahydrofuran, dimethylformamide and the like. In order to minimize side reactions, there is included in the reaction mixture a base to react with the acid halide released during the course of the reaction. Preferred bases are amines such as imidazole, pyridine, or triethylamine. The base is required in amounts equimolar to the amount of hydrogen halide liberated; however, generally several equivalents of the amine are employed. The reaction is stirred at from 0° C. to the reflux temperature of the reaction mixture and is complete in from ½ to 16 hours. The silyl group is removed by treatment of the silyl compound with anhydrous pyridine-hydrogen fluoride in tetrahydrofuran. The reaction is complete in from 3 to 24 hours at from 0° to 25° C. Alternatively, the silyl group may be removed by stirring the silylated compound in methanol catalyzed by an acid preferably a sulfonic acid monohydrate such as p-toluenesulfonic acid monohydrate. The reaction is complete in about 1 to 12 hours at from 0° to 50° C.

Another of the starting materials used in the preceding reaction scheme is the 4''- or 4'-epi-avermectin. The process consists generally of oxidizing the 4''- or 4'-position of the avermectin to the ketone by dissolving the oxidizing agent, preferably oxalyl chloride or trifluoroacetic anhydride and dimethylsulfoxide, in a chlorinated hydrocarbon solvent, such as methylene chloride, chloroform, trichloroethane and the like, preferably methylene chloride, with cooling from $-50°$ to $-80°$ C., and adding dropwise a solution of the avermectin compound to be oxidized, preferably an avermectin derivative with the 5-hydroxy position protected, in a chlorinated hydrocarbon solvent such as methylene chloride, chloroform, trichloroethane or the like, preferably methylene chloride. The addition is carried out over a period of from 15 minutes to 1 hour and then triethylamine is added dropwise over a period of from 1 to 15 minutes. The reaction mixture is allowed to warm to room temperature over a period of from 30 minutes to one hour. The 4''- or 4'-keto compound is isolated using techniques known to those skilled in the art. The 4''- or 4'-keto compound is then treated with a reducing agent such as sodium borohydride in an inert solvent such as methanol at from −25° to +10° C. for a period of from 15 minutes to 2 hours to give predominantly the 4''- or 4'-epi-avermectin compound, which is isolated using techniques known to those skilled in the art.

Other starting materials for the compounds of this invention are the 24- and 25-substituted avermectin derivatives. Their synthesis is described in Shih, et al., Tetrahedron Lett. 31: 3525 (1990) and Shih, et al., Tetrahedron Lett. 31: 3529 (1990). Starting with (I) or another avermectin derivative, the 23-oxo analog can be made as described in U.S. Pat. No. 4,289,760. For this purpose the 4''- and 5-hydroxy groups are protected as trialkylsilylethers, advantageously as the 4'',5-di-O-tert-butyldimethylsilylether. This is oxidized using the well known Swern oxidation conditions employing oxalyl chloride-dimethylsulfoxide followed by triethylamine as reagents, but other oxidants may also be employed. The 23-oxo group is ready for transformation into the silylenolether required for the cleavage of the bond between carbon 22 and 23. Reaction of the protected 23-ketone (II) with trimethylsilyl chloride in the presence of a strong base gives the desired 23-O-trimethylsilyl-22,23-en-23-ol ether derivative and simultaneously puts a trimethylsilyl group onto the tertiary C-7 hydroxy group (III). The selection of the base for this reaction is of crucial importance. Lithium bis(trimethylsilyl)amide is can form the desired silyl enol ether without any further side reactions. The newly formed 22,23-double bond of the trimethylsilyl enol ether reacts in the presence of four additional double bonds with a peroxy acid such as 3-chloroperoxybenzoic acid to form a 22,23-oxide intermediate (IV), which spontaneously rearranges to form the 22-hydroxy-23-oxo derivative (V). The 22,23-carbon bond of this intermediate be cleaved using lead tetraacetate as oxidating reagent to afford an intermediate where the C-22 is oxidized to an aldehyde and C-23 to a carboxylic acid (VI). This acid is still attached to C-21 of the macrolide ring through an acetal oxygen atom. Transacetalization in methanol with pyridinium tosylate as acid catalyst cleaves this bond and gives a C-21 epimeric mixture of an avermectin derivative which has lost carbon atoms 23 to 28, and has a methoxy and an aldehyde group attached to carbon atom 21 (VIIA and VIIB).

Starting with this intermediate, carbon synthons can be added to the C-22 aldehyde carbon atom. These synthons contain a protected hydroxy group at the appropriate position where they can react (after deprotection) with the C-21 carbon atom in order to complete the dioxaspirane ring and yield avermectin analogs with substitutions at the 24- and 25-position. To this end the aldehyde is reacted with a triphenyl phosphonium salt in a Wittig reaction in the presence of base, preferably potassium bis(trimethylsilyl)amide. The thus formed olefinic intermediate containing the double bond in the 22,23-position and a trimethylsilyl protected hydroxy group at the 25-position is now treated with pyridinium tosylate in anhydrous methanol, which accomplishes first the cleavage of the C-25-O-trimethylsilyl ether and then the transketalisation to form the dioxaspirane structure (VIII). Removal of the 4''-, 5-, and 7-O-protecting groups either with hydrofluoric acid-pyridine-tetrahydrofuran or with p-toluenesulfonic acid in methanol gives the desired 24,25-substituted starting materials.

The required phosphonium salts are obtained routinely by starting, for instance, with the readily available (S)-3-chloro-1-phenyl-1-propanol, converting it to the corresponding 3-iodo derivative (with sodium iodide in methylethyl ketone), protecting the hydroxy group as a trimethylsilyl ether (with bis(trimethylsilyl)-trifluoroacetamide), which then is reacted with triphenylphosphine to form the required phosphonium iodide. If the required substituted propanols are not available, they can be prepared from readily available 2-substituted acroleins, where the 2-substitutent corresponds to the eventual C-24 substituent of the avermectins.

Scheme I
Preparation of 24,25-Substituted-Starting Materials

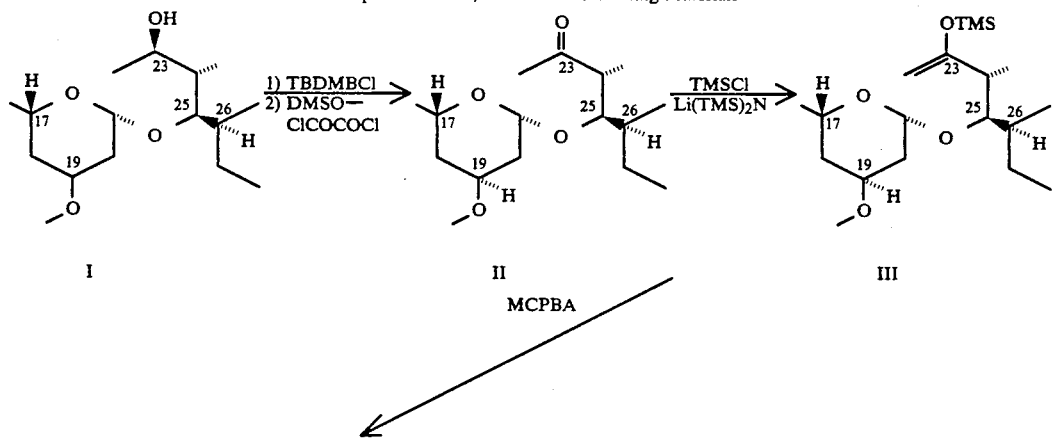

-continued
Scheme I
Preparation of 24,25-Substituted-Starting Materials

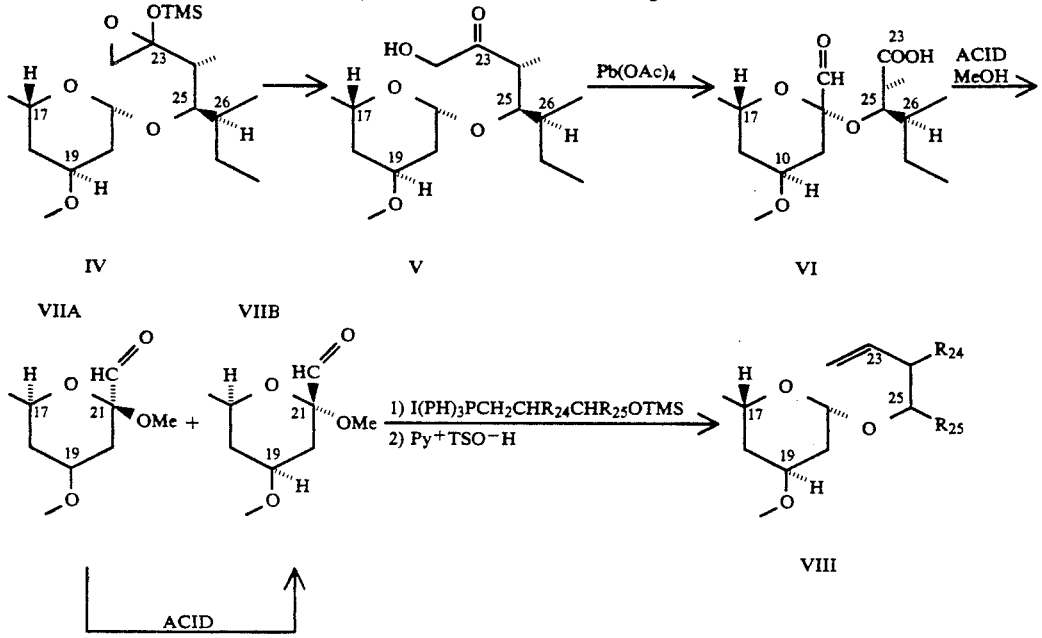

Key:
TBDMS = tert.-butyldimethylsilyl
TMS = trimethylsilyl
MCPBA = metachloroperbenzoic acid
DMSO = dimethylsulfoxide
ClCOCOCl = oxalyl chloride
Pb(OAc)$_4$ = lead tetracetate Hydrochloric acid addition to the double bond and reaction of the chloroaldehyde with a Grignard reagent RMgX, where R provides the eventual C-25 substitutent of the avermectins and X is halogen, provides the variously substituted chloropropanols. Other substituted propanols are prepared from 2-substituted malonate esters as further described in the preparations.

Another of the starting materials used in the foregoing reaction scheme are those in which the 22,23 double bond has been reduced to a single bond. The preferred catalyst for the selective hydrogenation of the 22,23 double bond is one having the formula:

[((R)$_3$P)$_3$RhY]

wherein R is loweralkyl, phenyl, or loweralkyl substituted phenyl and Y is halogen. The reduction is completely described in U.S. Pat. No. 4,199,569.

The other starting materials which are used in the above reaction scheme involve the preparation of the monosaccharide. The processes which may be used to prepare the monosaccharide derivatives of the avermectin compounds are described in U.S. Pat. No. 4,206,205. The reaction consists generally of treating the starting disaccharide with acid in an aqueous organic solvent mixture. Water concentration of from 0.1 to 20% by volume and acid concentrations of from about 0.01 to 0.1% will predominantly produce the monosaccharide.

A procedure for the preparation of the monosaccharide utilizes a 1% mineral acid solution in isopropanol at 20° to 40° C., preferably at room temperature, for from 6 to 24 hours. Mineral acids such as sulfuric, phosphoric, and the like may be employed.

In all cases the substitutent at the 25-position of the avermectin is inert to the reaction conditions and the presence of alkyl groups, alkenyl groups, cycloalkyl groups, cycloalkenyl groups and the like at this position will little affect the preparation, isolation, or reactivity of the avermectin derivative.

PREPARATION OF COMPOUNDS

The preparation of the novel compounds of this invention is best accomplished when the avermectin starting materials are protected at the 5-hydroxy position to avoid substitution at this position. With this position protected, the reactions may be carried out at the 4"- or 4'-positions without affecting the remainder of the molecule. The 5-hydroxy group is protected by a tert.-butyldimethylsilyl group before displacement at the 4"- or 4'-hydroxyl group has occurred. The 23-hydroxy group is less reactive and the 7-hydroxy group is very unreactive, and these need not be protected.

The preparation of the novel compounds requires that the avermectin starting materials are converted to derivatives with good leaving groups at the 4"- or 4'-position, preferably iodo- or alkyl-substituted sulfonyl groups, more preferably trifluoromethanesulfonyl- or iodo- groups. Subsequently, these leaving groups are displaced by sulfur-containing nucleophiles to obtain the desired 4"-deoxy-4"-substituted acyl- or alkyl-thio-avermectin derivatives, (which also may be modified further).

The 4"- or 4'-alkyl substituted sulfonyl intermediate is prepared from the 5-protected avermectin using the appropriate sulfonic anhydride or the appropriate sulfonyl chloride in an inert solvent such as a chlorinated hydrocarbon, tetrahydrofuran (THF), or ether, preferably methylene chloride, in the presence of base at −15° to 10° C. over a period of 15 minutes to 1 hour. The 4″- or 4′-alkyl substituted sulfonyl compound may be isolated using techniques known to those skilled in the art. Then the 4″- or 4′-sulfonylavermectin is substituted at the 4″- or 4′-position by sulfur-containing nucleophiles. The reaction is carried out at or near at room temperature in an inert solvent such as dimethylformamide (DMF), dimethylsulfoxide (DMSO), THF, chlorinated hydrocarbons, or ether, preferably DMF, with the desired thiol nucleophile, either the metallic thiol or a thiol with a base such as potassium carbonate at 0° to 25° C. over a period of 1 to 8 hours. Optionally, a catalyst such as 18-crown-6 (1,4,7,10,13,16-hexaoxocyclooctadecane) may be added. The products are isolated using known techniques.

There are two possible epimers at the 4″ or 4′-position; one with the stereochemistry exactly as in the natural avermectins with an equatorial (or α) substituent and one with the axial (or β) configuration. The latter is called 4″- or 4′-epi. The reaction with soft nucleophiles results predominantly in the product with the inverted configuration. The reaction with hard nucleophiles usually gives both compounds, which are separable, but since both possess high biological activities, they need not be separated. Both epimers are considered part of this invention, either separate or in a mixture.

Nucleophilic substitution of the leaving group can be also accomplished by iodine, by adding an iodine salt to a stirring solution of the avermectin substituted with a good leaving group at the 4″-position in DMF, DMSO, THF or a chlorinated hydrocarbon and allowing the reaction to stir at room temperature from 1 to 6 hours. The product is isolated using known techniques. The 4″-iodine atom can, in turn, be displaced by other nucleophiles, including other sulfur-containing nucleophiles.

Alternatively, compounds of this invention can be synthesized starting with the unprotected 4″-deoxy-4″-thio-avermectin derivative, prepared according to the procedures above. The 4″-thio-avermectin starting material is dissolved in a polar solvent such as dimethylformamide, dimethylsulfoxide, or methanol at room temperature. To this solution is added a base such as potassium carbonate, sodium hydride or potassium hydride, preferably anhydrous potassium carbonate, and the desired alkyl halide, preferably an alkyl iodide. Optionally, a catalyst such as 18-crown-6 may be added. After 2 to 24 hours, the reaction mixture is poured in to saturated brine and the product, the 4″-deoxy-4″-alkylthio-avermectin derivative, is isolated using known techniques.

The sulfur-containing 4′- and 4″-groups can be oxidized to the corresponding sulfinyl and sulfonyl groups in a solvent such as a chlorinated hydrocarbon, THF, ether, or lower alcohol, preferably, methylene chloride. An oxidizing agent such as a peracid, preferably m-chloroperbenzoic acid, is added to a solution of the 4″- or 4′-substituted avermectin. By varying the temperature (from −30° C. to room temperature) and the number of equivalents of oxidizing agent, the relative yields of the sulfoxide and sulfone can be controlled. The products are separated and isolated using techniques known to those skilled in the art.

Further modifications of the side chain can be accomplished when a thio-alcohol is used as the nucleophile. The hydroxyl group of the alcohol on the sulfur-containing side chain can undergo any the reactions and chemistry that is possible at the 4″- or 4′-hydroxy group, including, but not limited to, those described herein.

Following the desired substitution and modification at the 4″-position, the 5-hydroxy group is deprotected, and, if desired, modifications of the molecule at the 5-position can occur.

The foregoing reactions carried out at the 4″-position of the avermectin can be carried out at the 4′-position of the avermectin monosacchoride to affect the correspondingly substituted monosacchoride derivatives.

BIOLOGICAL ACTIVITIES OF THE INSTANT COMPOUNDS

The novel compounds of this invention are potent endo- and ecto-antiparasitic agents against parasites particularly helminths, ectoparasites, insects, and acarides, infecting man, animals and plants, thus having utility in human and animal health, agriculture and pest control in household and commercial areas.

The disease or group of diseases described generally as helminthiasis is due to infection of an animal host with parasitic worms known as helminths. Helminthiasis is a prevalent and serious economic problem in domesticated animals such as swine, sheep, horses, cattle, goats, dogs, cats, fish, buffalo, camals, llamas, reindeer, laboratory animals, fur-bearing animals, zoo animals and exotic species and poultry. Among the helminths, the group of worms described as nematodes causes widespread and often times serious infection in various species of animals. The most common genera of nematodes infecting the animals referred to above are Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Habronema, Druschia, Heterakis, Toxocara, Ascaridia, Oxyuris, Ancylostoma, Uncinaria, Toxascaris and Parascaris. Certain of these, such as Nematodirus, Cooperia, and Oesophagostomum attack primarily the intestinal tract while others, such as Haemonchus and Ostertagia, are more prevalent in the stomach while still others such as Dictyocaulus are found in the lungs. Still other parasites may be located in other tissues and organs of the body such as the heart and blood vessels, subcutaneous and lymphatic tissue and the like. The parasitic infections known as helminthiases lead to anemia, malnutrition, weakness, weight loss, severe damage to the walls of the intestinal tract and other tissues and organs and, if left untreated, may result in death of the infected host. The compounds of this invention have unexpectedly high activity against these parasites, and in addition are also active against Dirofilaria in dogs and cats, Nematospiroides, Syphacia, Aspiculuris in rodents, arthropod ectoparasites of animals and birds such as ticks, mites, lice, fleas, blowflies, in sheep Lucilia sp., biting insects and such migrating diperous larvae as Hypoderma sp. cattle, Gastrophilus in horses, and Cuterebra sp. in rodents and nuisance flies including blood feeding flies and filth flies.

The instant compounds are also useful against parasites which infect humans. The most common genera of parasites of the gastro-intestinal tract of man are Ancylostoma, Necator, Ascaris, Strongyloides, Trichinella, Capillaria, Trichuris, and Enterobius. Other medically important genera of parasites which are found in the blood or other tissues and organs outside the gastrointestinal tract are the filiarial worms such as Wuchereria, Brugia, Onchocerca and Loa, Dracunuculus and extra-intestinal stages of the intestinal worms Strongyloides and Trichinella. The compounds are also of value against arthropods parasitizing man, biting insects and other dipterous pests causing annoyance to man.

The compounds are also active against household pests such as the cockroach, Blatella sp., clothes moth, Tineola sp., carpet beetle, Attagenus sp., the housefly *Musca domestica* as well as fleas, house dust mites, termites and ants.

The compounds are also useful against insect pests of stored grains such as Tribolium sp., Tenebrio sp. and of agricultural plants such as aphids, (Acyrthiosiphon sp.); against migratory orthopterans such as locusts and immature stages of insects living on plant tissue. The compounds are useful as a nematocide for the control of soil nematodes and plant parasites such as Meloidogyne sp. which may be of importance in agriculture. The compounds are also highly useful in treating acerage infested with fire ant nests. The compounds are scattered above the infested area in low levels in bait formulations which are brought back to the nest. In addition to a direct-but-slow onset toxic effect on the fire ants, the compound has a long-term effect on the nest by sterilizing the queen which effectively destroys the nest.

The compounds of this invention may be administered in formulations wherein the active compound is intimately admixed with one or more inert ingredients and optionally including one or more additional active ingredients. The compounds may be used in any composition known to those skilled in the art for administration to humans and animals, for application to plants and for premise and area application to control household pests in either a residential or commercial setting. For application to humans and animals to control internal and external parasites, oral formulations, in solid or liquid or parenteral liquid, implant or depot injection forms may be used. For topical application dip, spray, powder, dust, pour-on, spot-on, jetting fluid, shampoos, collar, tag or harness, may be used. For agricultural premise or area application, liquid spray, powders, dust, or bait forms may be used. In addition "feed-through" forms may be used to control nuisance flies that feed or breed in animal waste. The compounds are formulated, such as by encapsulation, to leave a residue of active agent in the animal waste which controls filth flies or other arthropod pests.

These compounds may be administered orally in a unit dosage form such as a capsule, bolus or tablet, or as a liquid drench where used as an anthelmintic in mammals. The drench is normally a solution, suspension or dispersion of the active ingredient usually in water together with a suspending agent such as bentonite and a wetting agent or like excipient. Generally, the drenches also contain an antifoaming agent. Drench formulations generally contain from about 0.001 to 0.5% by weight of the active compound. Preferred drench formulations may contain from 0.01 to 0.1% by weight. The capsules and boluses comprise the active ingredient admixed with a carrier vehicle such as starch, talc, magnesium stearate, or di-calcium phosphate.

Where it is desired to administer the instant compounds in a dry, solid unit dosage form, capsules, boluses or tablets containing the desired amount of active compound usually are employed. These dosage forms are prepared by intimately and uniformly mixing the active ingredient with suitable finely divided diluents, fillers, disintegrating agents, and/or binders such as starch, lactose, talc, magnesium stearate, vegetable gums and the like. Such unit dosage formulations may be varied widely with respect to their total weight and content of the antiparasitic agent depending upon factors such as the type of host animal to be treated, the severity and type of infection and the weight of the host.

When the active compound is to be administered via an animal feedstuff, it is intimately dispersed in the feed or used as a top dressing or in the form of pellets or liquid which may then be added to the finished feed or optionally fed separately. Alternatively, feed based individual dosage forms may be used such as a chewable treat. Alternatively, the antiparasitic compounds of this invention may be administered to animals parenterally, for example, by intraruminal, intramuscular, intravascular, intratracheal, or subcutaneous injection in which the active ingredient is dissolved or dispersed in a liquid carrier vehicle. For parenteral administration, the active material is suitably admixed with an acceptable vehicle, preferably of the vegetable oil variety such as peanut oil, cotton seed oil and the like. Other parenteral vehicles such as organic preparation using solketal, glycerol formal, propylene glycol, and aqueous parenteral formulations are also used. The active compound or compounds are dissolved or suspended in the parenteral formulation for administration; such formulations generally contain from 0.0005 to 5% by weight of the active compound.

Although the antiparasitic agents of this invention find their primary use in the treatment and/or prevention of helminthiasis, they are also useful in the prevention and treatment of diseases caused by other parasites, for example, arthropod parasites such as ticks, lice, fleas, mites and other biting arthropods in domesticated animals and poultry. They are also effective in treatment of parasitic diseases that occur in other animals including humans. The optimum amount to be employed for best results will, of course, depend upon the particular compound employed, the species of animal to be treated and the type and severity of parasitic infection or infestation. Generally good results are obtained with our novel compounds by the oral administration of from about 0.001 to 10 mg per kg of animal body weight, such total dose being given at one time or in divided doses over a relatively short period of time such as 1-5 days. With the preferred compounds of the invention, excellent control of such parasites is obtained in animals by administering from about 0.025 to 0.5 mg per kg of body weight in a single dose. Repeat treatments are given as required to combat re-infections and are dependent upon the species of parasite and the husbandry techniques being employed. The techniques for administering these materials to animals are known to those skilled in the veterinary field.

When the compounds described herein are administered as a component of the feed of the animals, or dissolved or suspended in the drinking water, compositions are provided in which the active compound or compounds are intimately dispersed in an inert carrier or diluent. By inert carrier is meant one that will not react with the antiparasitic agent and one that may be administered safely to animals. Preferably, a carrier for feed administration is one that is, or may be, an ingredient of the animal ration.

Suitable compositions include feed premixes or supplements in which the active ingredient is present in relatively large amounts and which are suitable for direct feeding to the animal or for addition to the feed either directly or after an intermediate dilution or blending step. Typical carriers or diluents suitable for such compositions include, for example, distillers' dried grains, corn meal, citrus meal, fermentation residues, ground oyster shells, wheat shorts, molasses solubles, corn cob meal, edible bean mill feed, soya grits, crushed limestone and the like. The active compounds are intimately dispersed throughout the carrier by methods such as grinding, stirring, milling or tumbling. Compositions containing from about 0.005 to 2.0% weight of the active compound are particularly suitable as feed premixes. Feed supplements, which are fed directly to the animal, contain from about 0.0002 to 0.3% by weight of the active compounds.

Such supplements are added to the animal feed in an amount to give the finished feed the concentration of active compound desired for the treatment and control of parasitic diseases. Although the desired concentration of active compound will vary depending upon the factors previously mentioned as well as upon the particular compound employed, the compounds of this invention are usually fed at concentrations of between 0.00001 to 0.002% in the feed in order to achieve the desired antiparasitic result.

In using the compounds of this invention, the individual compounds may be prepared and used in that form. Alternatively, mixtures of the individual compounds may be used, or other active compounds not related to the compounds of this invention.

The compounds of this invention are also useful in combatting agricultural pests that inflict damage upon crops while they are growing or while in storage. The compounds are applied using known techniques as sprays, dusts, emulsions and the like, to the growing or stored crops to effect protection from such agricultural pests.

The following examples are provided in order that this invention might be more fully understood; they are not to be construed as limitative of the invention.

The avermectin derivatives prepared in the following examples are generally isolated as amorphous solids and not as crystalline solids. They are thus characterized analytically using techniques such as mass spectrometry, nuclear magnetic resonance spectrometry and the like. Being amorphous, the compounds are not characterized by sharp melting points; however, the chromatographic and analytical methods employed indicate that the compounds are pure.

EXAMPLE 1

4''-Deoxy-4''-epi-methylthio-avermectin B1a/B1b

Step A Preparation of the Intermediate 4''-O-Trifluoromethanesulfonyl-5-O-tert.-butyldimethylsilyl-avermectin B1a/B1b To a stirring solution of 5-O-tert.-butyldimethylsilyl-avermectin B1a/B1b (6000 mg, 6.09 mmol) in dry methylene chloride ($CH_2Cl_2$, 30.0 mL), N,N-diisopropylethylamine (6.353 mL, 36.54 mmol) was added followed by 4-dimethylaminopyridine (DMAP, 4458 mg, 36.54 mmol). The solution was cooled to 0° C. under nitrogen, and trifluoromethanesulfonic anhydride ($Tf_2O$, 4.097 mL, 24.36 mmol) was added over 1 minute. After 30 minutes at 0° C., the reaction mixture was partitioned between ice/water and methylene chloride. The methylene chloride extracts were dried over magnesium sulfate, filtered and concentrated in vacuo. The crude product was purified through a plug of silica gel using hexane-ethyl acetate (1:1). The product was concentrated to an oil and lyophilized from benzene. The pure product, 4''-O-trifluoromethanesulfonyl-5-O-tert.-butyldimethylsilyl-avermectin B1a/B1b, was characterized by nuclear magnetic resonance spectroscopy. Yield 5.01 g.

Step B Preparation of 4''-Deoxy-4''-epi-methylthio-5-O-tert.-butyldimethylsilyl-avermectin B1a/B1b Gaseous methane thiol was bubbled moderately fast through dry dimethylformamide (DMF, 4 mL) for 2.0 minutes, followed by the addition of potassium carbonate (231 mg, 1.671 mmol). After the solution was cooled to 0° C. under nitrogen, 4''-O-trifluoromethanesulfonyl-5-O-tert.-butyldimethylsilyl-avermectin B1a/B1b (1244 mg, 1.113 mmol), prepared according to the procedures above, was added. After 20 minutes, the reaction mixture was allowed to warm to room temperature. After stirring at room temperature for 2 hours, the reaction mixture was partitioned between a solution of saturated sodium bicarbonate and methylene chloride. The methylene chloride extracts were washed with water, dried over magnesium sulfate, filtered, and concentrated to an oil. The crude product (2.1 g, brown oil) was purified by flash silica column chromatography using hexane-ethyl acetate (3:1) as eluent. The fractions containing product were pooled, and the pure product, 4''-deoxy-4''-epi-methylthio-5-O-tert.-butyldimethylsilyl-avermectin B1a/B1b, was characterized by nuclear magnetic resonance spectroscopy and purity was determined by reversed-phase high pressure liquid chromatography. Yield 175 mg.

Step C Preparation of 4''-deoxy-4''-epi-methylthio-avermectin B1a/B1b

4''-Deoxy-4''-epi-methylthio-5-O-tert.-butyldimethylsilyl-avermectin B1a/B1b (284 mg, 0.28 mmol), prepared according to the procedures above, was dissolved in tetrahydrofuran (THF, 4 mL). To this was added 2 mL of a HF-pyridine solution (25 g HF-pyridine, 10 mL pyridine, 28 mL THF). After 5 hours, the reaction mixture was cooled to 0° C., diluted with ether (2 mL), and poured into cold water (15–20 mL). Additional ether was added. The aqueous layer was removed, and the organic layer was washed with a saturated aqueous sodium bicarbonate solution (5–10 mL), which was added to the water extract. Additional sodium bicarbonate was added to the combined aqueous washings until foaming ceased. The aqueous layer was extracted with ether, and all ether extracts were combined, washed with water, dried over magnesium sulfate, filtered, and concentrated to a yellow oil. (292 mg). The crude product was purified by flash silica gel chromatography using hexane-ethyl acetate (65:35). The fractions containing product were pooled, concentrated in vacuo, and lyophilized from benzene. The pure product, 4''-deoxy-4''-epi-methylthio-avermectin B1a/B1b, was characterized by nuclear magnetic resonance spectroscopy, and purity was determined by reversed-phase high pressure liquid chromatography.

EXAMPLE 2

4″-Deoxy-4″-methylthio-avermectin B1a/B1b

Step A Preparation of the Intermediate 4″-O-epi-Trifluoromethanesulfonyl-5-O-tert.-butyldimethylsilyl-avermectin B1a/B1b To a stirring solution of 5-O-tert.-butyldimethylsilyl-4″-epi-avermectin B1a/B1b (4000 mg, 4.06 mmol) in dry methylene chloride (20.0 mL), N,N-diisopropylethylamine (4.325 mL, 24.36 mmol) was added followed by 4-dimethylaminopyridine (DMAP, 2972 mg, 24.36 mmol). The solution was cooled to 0° C. under nitrogen, and trifluoromethanesulfonic anhydride (Tf$_2$O, 2.731 mL, 16.24 mmol) was added over 1 minute. After 30 minutes at 0° C., the reaction mixture was partitioned between ice/water and methylene chloride. The methylene chloride extracts were dried with magnesium sulfate, filtered and concentrated in vacuo. The crude product was purified through a plug of silica gel using hexane-ethyl acetate (1:1). The product was concentrated to an oil and lyophilized from benzene. The pure product, 4″-epi-O-trifluoromethanesulfonyl-5-O-tert.-butyldimethylsilyl-avermectin B1a/B1b, was characterized by nuclear magnetic resonance spectroscopy. Yield 3655 mg of light brown/orange foam.

Step B Preparation of 4″-Deoxy-4″-methylthio-5-O-tert.-butyldimethylsilyl-avermectin B1a/B1b Gaseous methane thiol was bubbled moderately fast through dry DMF (4 mL) for 2 minutes, followed by the addition of potassium carbonate (242 mg, 1.755 mmol). After the solution was cooled to 0° C. under nitrogen, 4″-epi-O-trifluoromethanesulfonyl-5-O-tert.-butyldimethylsilyl-avermectin B1a/B1b (1308 mg, 1.170 mmol) was added. After 20 minutes, the reaction mixture was allowed to warm to room temperature. After stirring at room temperature for 2 hours, the reaction mixture was partitioned between a solution of saturated sodium bicarbonate and methylene chloride. The methylene chloride extracts were washed with water, dried over magnesium sulfate, filtered, concentrated to an oil, and stored under vacuum 16 hours. The crude product (1386 mg) was purified by flash silica column chromatography using 3:1 hexane-ethyl acetate. The fractions containing product were pooled, and the pure product, 4″-deoxy-4″-methylthio-5-O-tert.-butyldimethylsilyl-avermectin B1a/B1b, was characterized by nuclear magnetic resonance spectroscopy and purity was determined by reversed-phase high pressure liquid chromatography. Yield 894 mg.

Step C Preparation of 4″-Deoxy-4″-methylthio-avermectin B1a/B1b

4″-Deoxy-4″-methylthio-5-O-tert.-butyldimethylsilyl-avermectin B1a/B1b (894 mg, 0.88 mmol), prepared according to the procedures outlined above, was dissolved in 4 mL THF. To this solution was added 2 mL of a HF-pyridine solution (25 g HF-pyridine, 10 mL pyridine, 28 mL THF). After 5 hours, the reaction mixture was cooled to 0° C., diluted with ether (2 mL), and poured into cold water (15-20 mL). Additional ether was added. The aqueous layer was removed, and the organic layer was washed with a saturated aqueous sodium bicarbonate solution (5-10 mL), which was added to the water extract. Additional sodium bicarbonate was added to the combined aqueous washings until foaming ceased. The aqueous layer was extracted with ether, and all ether extracts were combined, washed with water, dried over magnesium sulfate, filtered, and concentrated to a yellow oil. The crude product (783 mg), was purified by flash silica gel chromatography using hexane-ethyl acetate (65:35). The fractions containing product were pooled, concentrated in vacuo, and lyophilized from benzene. The pure product, 4″-deoxy-4″-methylthio-avermectin B1a/B1b (458 mg), was characterized by nuclear magnetic resonance spectroscopy and purity was determined by reversed-phase high pressure liquid chromatography.

EXAMPLE 3

4″-Deoxy-4″-epi-methylsulfinyl-avermectin B1a/B1b and 4″-Deoxy-4″-epi-methylsulfonyl-avermectin B1a/B1b 4″-deoxy-4″-epi-methylthio-avermectin B1a/B1b (289 mg, 0.320 mmol), prepared according to the procedures in Example 1, was dissolved in dry methylene chloride (6 mL), and cooled under nitrogen to −15° C. To the cooled solution was added 85% m-chloroperbenzoic acid (97 mg, 0.48 mmol). After 30 minutes, the solution was allowed to warm to 0° C. for 30 minutes, and then allowed to warm to room temperature. Additional m-chloroperbenzoic acid (22 mg, 0.11 mmol) was added. After 30 minutes, the reaction mixture was partitioned between a saturated aqueous sodium bicarbonate solution (20 mL) containing sodium thiosulfate (2 g) and methylene chloride (30 mL). The methylene chloride extracts were dried over magnesium sulfate, filtered and concentrated to an oily solid. The crude products were purified by preparative thin layer silica chromatography using ethyl acetate-acetone (9:1). Both the 4″-deoxy-4″-epi-methylsulfinyl-avermectin B1a/B1b and 4″-deoxy-4″-epi-methylsulfonyl-avermectin B1a/B1b were isolated in pure form, and each was concentrated separately to an oily glass. The pure products were lyophilized from benzene and characterized by nuclear magnetic resonance spectroscopy and mass spectroscopy (sulfoxide: (M+7)=925; sulfone: (M+7)=941). Purity was assessed by reversed-phase high pressure liquid chromatography. Yield: sulfoxide, 68 mg; sulfone, 98 mg.

EXAMPLE 4

4″-Deoxy-4″-methylsulfinyl-avermectin B1a/B1b and 4″-Deoxy-4″-methylsulfonyl-avermectin B1a/B1b 4″-Deoxy-4″-methylthio-avermectin B1a/B1b (614 mg, 0.680 mmol), prepared according to the procedures in Example 2, was dissolved in dry methylene chloride (10 mL), and cooled under nitrogen to −15° C. To the cooled solution was added 60% m-chloroperbenzoic acid (300 mg, 1.043 mmol). After 10 minutes, solution was allowed to warm to 0° C. for 20 minutes, and then allowed to warm to room temperature. The reaction mixture was partitioned between a saturated aqueous sodium bicarbonate solution containing sodium sulfate and methylene chloride. The methylene chloride extracts were dried over magnesium sulfate, filtered and concentrated to an oily solid. The crude products (660 mg) were purified by flash silica gel chromatography using ethyl acetate-hexane (3:1). Both the 4″-deoxy-4″-methylsulfinyl-avermectin B1a/B1b and 4″-deoxy-4″-methylsulfonyl-avermectin B1a/B1b were isolated, and each was concentrated separately to an oily glass. The pure products were lyophilized from benzene and characterized by nuclear magnetic resonance spectroscopy and mass spectroscopy (sulfoxide: (M+7)=925; sulfone: (M+7)=941). Purity was assessed by reversed-phase high pressure liquid chromatography. Yield: sulfoxide, 132 mg; sulfone, 121 mg.

EXAMPLE 5

Preparation and separation of
(+)-4"-Deoxy-4"-methylsulfinyl-avermectin B1a/B1b
and (−)-4"-Deoxy-4"-methyl-sulfinyl-avermectin
B1a/B1b 4"-Deoxy-4"-methylthio-avermectin B1a/B1b (100 mg, 0.111 mmol), prepared according to the procedures in Example 2, was dissolved in 1 mL methanol and stirred at room temperature. To this solution was added periodic acid ($H_5IO_6$, 250 mg, 1.096 mmol). After 3 hours, 1 mL of a saturated solution of sodium bicarbonate, 1 mL of water and 1 mL of a saturated aqueous solution of sodium chloride were added to the reaction vessel. The solution was transferred to a separatory funnel and extracted with ethyl acetate. The organic extracts were combined, dried over magnesium sulfate, filtered, and concentrated in vacuo to give 330 mg crude material. This crude product was purified by flash silica gel chromatography using ethyl acetate-acetone (9:1).

The sulfoxide diastereomers were separated and purified by preparative reversed-phase high pressure liquid chromatography using a Vydac $C_{18}$ column and methanol-water (80:20) as eluant. fractions containing product were pooled and lyophilized. Both sulfoxide diastereomers were isolated. Yield: 49 mg isomer A (faster moving by HPLC), and 52 mg isomer B (slower moving by HPLC). Purity was determined by analytical reversed-phase high pressure liquid chromatography and the products were characterized by nuclear magnetic resonance and mass spectroscopy, (M+7)=925.

EXAMPLE 6

4"-Deoxy-4"-epi-methylsulfinyl-5-oximino-avermectin B1a/B1b

Step A Preparation of 4"-deoxy-4"-epi-methylsulfinyl-5-keto-avermectin B1a/B1b

To a solution of 4"-deoxy-4"-epi-methylsulfinyl-avermectin B1a/B1b (30 mg, 0.033 mmol), prepared according to Example 3, in ethyl acetate (200 μL), manganese(IV) oxide (200 mg, 2.3 mmol) was added. After 90 minutes, the reaction mixture was filtered through a plug of silica gel using ethyl acetate-acetone (7:3). The product was concentrated to a constant weight. The pure product, 4"-deoxy-4"-epi-methylsulfinyl-5-keto-avermectin B1a/B1b, was characterized by nuclear magnetic resonance spectroscopy and purity was assessed by reversed-phase high pressure liquid chromatography.

Step B Preparation of 4"-deoxy-4"-epi-methylsulfinyl-5-oximino-avermectin B1a/B1b The starting material, 4"-deoxy-4"-epi-methylsulfinyl-5-keto-avermectin B1a/B1b, was prepared according to the general procedures outlined above. To a solution of the starting material (18 mg, 0.019 mmol) in ethyl acetate (1 mL) was added zinc chloride ($ZnCl_2$, 70 μL of a 1.0M solution in diethyl ether, 0.070 mmol), followed by O-(trimethylsilyl)-hydroxylamine (20 μL, 0.164 mmol). After two hours, the reaction mixture was partitioned between an aqueous saturated sodium bicarbonate solution and diethyl ether. The ether layer was washed with water, dried over sodium sulfate, filtered, and concentrated to a foam. The crude product was purified through a silica plug using methanol-methylene chloride, and was concentrated. Pure 4"-deoxy-4"-epi-methylsulfinyl-5-oximino-avermectin B1a/B1b was lyophilized from benzene and characterized by nuclear magnetic resonance spectroscopy and mass spectroscopy, (M+7)=938. Purity was assessed by high pressure liquid chromatography. Yield 16 mg.

EXAMPLE 7

4"-Deoxy-4"-methylsulfonyl-5-oximino-avermectin B1a/B1b

Step A Preparation of 4"-deoxy-4"-methylsulfonyl-5-keto-avermectin B1a/B1b

To a solution of 4"-deoxy-4"-methylsulfonylavermectin B1a/B1b (30 mg; 0.032 mmol), prepared according to the procedures in Example 4, in ethyl acetate (200 μL), manganese(IV) oxide (200 mg, 2.3 mmol) was added. After 90 minutes, the reaction mixture was filtered through a silica plug using ethyl acetate-hexane (1:1). The product was concentrated to a constant weight. Pure 4"-deoxy-4"-methyl-sulfonyl-5-keto-avermectin B1a/B1b was characterized by nuclear magnetic resonance spectroscopy and purity was assessed by reversed-phase high pressure liquid chromatography. Yield 20 mg.

Step B Preparation of 4"-deoxy-4"-methylsulfonyl-5-oximino-avermectin B1a/B1b

The starting material, 4"-deoxy-4"-methylsulfonyl-5-keto-avermectin B1a/B1b, was prepared according to the general procedures outlined above. To a solution of the starting material (20 mg, 0.021 mmol) in ethyl acetate (1 mL) was added zinc chloride ($ZnCl_2$, 70 μL of a 1.0M solution in diethyl ether, 0.070 mmol), followed by O-(trimethylsilyl)hydroxylamine (20 μL, 0.164 mmol). After two hours the reaction mixture was partitioned between an aqueous solution of sodium bicarbonate and diethyl ether. The ether layer was washed with water, dried over sodium sulfate, filtered and concentrated to a foam. The crude product was purified through a silica gel plug using methanol-methylene chloride (2:98), and was concentrated in vacuo. Pure 4"-deoxy-4"-methylsulfonyl-5-oximino-avermectin B1a/B1b was lyophilized from benzene and characterized by nuclear magnetic resonance spectroscopy and mass spectroscopy, (M+7)=954. Purity was assessed by reversed-phase high pressure liquid chromatography. Yield 16 mg.

EXAMPLE 8

4"-Deoxy-4"-epi-methylthio-5-oximino-avermectin B1a/B1b

Step A Preparation of 4"-deoxy-4"-epi-methylthio-5-keto-avermectin B1a/B1b

To a solution of 4"-deoxy-4"-epi-methylthioavermectin B1a/B1b (30 mg, 0.033 mmol), prepared according to Example 1, in ethyl acetate (200 μL), manganese(IV) oxide (200 mg, 2.3 mmol) was added. After 30 minutes, the reaction mixture was filtered through a silica plug using ethyl acetate-hexane (1:1). The product was concentrated to a constant weight. The pure product, 4"-deoxy-4"-epi-methylthio-5-keto-avermectin B1a/B1b, was characterized by nuclear magnetic resonance spectroscopy, and purity was assessed by reversed-phase high pressure liquid chromatography. Yield 24 mg.

Step B Preparation of 4"-deoxy-4"-epi-methylthio-5-oximino-avermectin B1a/B1b, was prepared according to the general procedures outlined above. To a solution of the starting material (24 mg, 0.027 mM) in ethyl acetate (1 mL) was added zinc chloride (70 μL of a 1.0M solution in diethyl ether, 0.070 mmol), followed by O-(trimethylsilyl)hydroxylamine (20 μL, 0.164 mmol). After two hours the reaction mixture was partitioned between an aqueous solution of sodium bicarbonate and diethyl ether. The ether layer was washed with water, dried over sodium sulfate, filtered and concentrated to a foam. The crude product was purified through a silica gel plug using methanol-methylene chloride (2:98) and was concentrated. Pure 4"-deoxy-4"-epi-methylthio-5-oximino-avermectin B1a/B1b was lyophilized from benzene and characterized by nuclear magnetic resonance spectroscopy and mass spectroscopy (M+7)=922. Purity was assessed by reversed-phase high pressure liquid chromatography. Yield 23 mg.

EXAMPLE 9

4"-Deoxy-4"-methylthio-5-oximino-avermectin B1a/B1b

Step A Preparation of 4"-deoxy-4"-methylthio-5-ketoavermectin B1a/B1b

To a solution of 4"-deoxy-4"-methylthioavermectin B1a/B1b (30 mg, 0.033 mmol), prepared according to Example 2, in ethyl acetate (200 μL), manganese(IV) oxide (200 mg, 2.3 mmol) was added. After 30 minutes, the reaction mixture was filtered through a silica plug using ethyl acetate-hexane (1:1). The product was concentrated to a constant weight. The pure product, 4"-deoxy-4"-methylthio-5-keto-avermectin B1a/B1b, was characterized by nuclear magnetic resonance spectroscopy and purity was assessed by reversed high pressure liquid chromatography. Yield 25 mg.

Step B Preparation of 4"-deoxy-4"-methylthio-5-oximino-avermectin B1a/B1b

The starting material, 4"-deoxy-4"-methylthio-5-keto-avermectin B1a/B1b, was prepared according to the general procedures outlined above. To a solution of the starting material (24 mg, 0.027 mmol) in ethyl acetate (1 mL) was added zinc chloride (70 μL of a 1.0M solution in diethyl ether, 0.070 mmol), followed by O-(trimethylsilyl)hydroxylamine (20 μL, 0.164 mmol). After two hours the reaction mixture was partitioned between an aqueous solution of sodium bicarbonate and diethyl ether. The ether layer was washed with water, dried over sodium sulfate, filtered, and concentrated to a foam. The crude product was purified through a silica gel plug using methanol-methylene chloride (2:98), and was concentrated. The product was lyophilized from benzene and characterized by nuclear magnetic resonance spectroscopy and mass spectroscopy (M+7)=922. Purity was assessed by reversed-phase high pressure liquid chromatography. Yield 22 mg.

EXAMPLE 10

4"-Deoxy-4"-epi-methylsulfonyl-5-oximino-avermectin B1a/B1b

Step A Preparation of 4"-deoxy-4"-epi-methylsulfonyl-5-keto-avermectin B1a/B1b

To a solution of 4"-deoxy-4"-epi-methylsulfonyl-avermectin B1a/B1b (30 mg, 0.032 mmol), prepared according to the procedures in Example 3, in ethyl acetate (200 μL), manganese(IV) oxide (200 mg, 2.3 mmol) is added. After 90 minutes, the reaction mixture is filtered through a silica plug using ethyl acetate-hexane (1:1). The product is concentrated to a constant weight. Pure 4"-deoxy-4"-epi-methylsulfonyl-5-keto-avermectin B1a/B1b is characterized by nuclear magnetic resonance spectroscopy and purity is determined by reversed-phase high pressure liquid chromatography.

Step B Preparation of 4"-deoxy-4"-epi-methylsulfonyl-5-oximino-avermectin B1a/B1b The starting material, 4"-deoxy-4"-epi-methylsulfonyl-5-keto-avermectin B1a/B1b, is prepared according to the general procedures outlined above. To a solution of the starting material (20 mg, 0.021 mmol) in ethyl acetate (1 mL) is added zinc chloride (70 μL of a 1.0M solution in diethyl ether, 0.070 mmol), followed by O-(trimethylsilyl)hydroxylamine (20 μL, 0.164 mmol). After two hours the reaction mixture is partitioned between an aqueous solution of sodium bicarbonate and diethyl ether. The ether layer is washed with water, dried over sodium sulfate, filtered and concentrated to a foam. The crude product is purified through a silica gel plug using methanol-methylene chloride (2:98), and is concentrated in vacuo. Pure 4"-deoxy-4"-epi-methylsulfonyl-5-oximino-avermectin B1a/B1b is lyophilized from benzene and characterized by nuclear magnetic resonance spectroscopy and purity is determined by reversed-phase high pressure liquid chromatography.

EXAMPLE 11

4"-Deoxy-4"-methylsulfinyl-5-oximino-avermectin B1a/B1b

Step A Preparation of 4"-deoxy-4"-methylsulfinyl-5-keto-avermectin B1a/B1b

To a solution of 4"-deoxy-4"-methylsulfinylavermectin B1a/B1b (30 mg, 0.033 mmol), prepared according to Example 4, in ethyl acetate (200 uL), manganese (IV) oxide (200 mg, 2.3 mmol) is added. After 90 minutes, the reaction mixture is filtered through a plug of silica gel using ethyl acetate-acetone (7:3). The product is concentrated to a constant weight. The pure product, 4"-deoxy-4"-epi-methyl-sulfinyl-5-keto-avermectin B1a/B1b, is characterized by nuclear magnetic resonance spectroscopy and purity is assessed by reversed-phase high pressure liquid chromatography.

Step B Preparation of 4"-deoxy-4"-methylsulfinyl-5-oximino-avermectin B1a/B1b

The starting material, 4"-deoxy-4"-methylsulfinyl-5-keto-avermectin B1a/B1b, is prepared according to the general procedures outlined above. To a solution of the starting material (18 mg, 0.019 mmol) in ethyl acetate (1 mL) is added zinc chloride (70 μL of a 1.0M solution in diethyl ether, 0.070 mmol), followed by O-(trimethylsilyl)hydroxylamine (20 μL, 0.164 mmol). After two hours, the reaction mixture is partitioned between an aqueous saturated sodium bicarbonate solution and diethyl ether. The ether layer is washed with water, dried over sodium sulfate, filtered, and concentrated to a foam. The crude product is purified through a silica gel plug using methanol-methylene chloride, and is concentrated in vacuo. Pure 4"-deoxy-4"-methylsulfinyl-5-oximino-avermectin B1a/B1b is lyophilized from benzene and characterized by nuclear magnetic resonance spectroscopy and purity is assessed by reversed-phase high pressure liquid chromatography.

EXAMPLE 12

4''-Deoxy-4''-octylthio-avermectin B1a/B1b and

4''-Deoxy-4''-epi-octylthio-avermectin B1a/B1b

Step A Preparation of 4''-Deoxy-4''-octylthio-5-O-tert.-butyldimethylsilyl-avermectin B1a/B1b and 4''-Deoxy-4''-epi-octylthio-5-O-tert.-butyldimethylsilyl-avermectin B1a/B1b To a stirring, room temperature solution of 4''-O-trifluoromethanesulfonyl-5-O-tert.-butyldimethylsilyl-avermectin B1a/B1b (100 mg, 0.089 mmol) in dimethylformamide (DMF, 1 mL) was added n-octyl mercaptan (65 μL, 0.447 mmol) and potassium carbonate (62 mg, 0.447 mmol). After 2.5 hours, the reaction mixture was partitioned between a saturated sodium bicarbonate solution and ethyl acetate. The ethyl acetate extract was dried over magnesium sulfate, concentrated in vacuo, and purified by preparative thin-layer silica gel chromatography using hexane-ethyl acetate (85:15). Both epimeric products, 4''-deoxy-4''-octylthio-5-O-tert.-butyldimethylsilyl-avermectin B1a/B1b and 4''-deoxy-4''-epi-octylthio-5-O-tert.-butyldimethylsilyl-avermectin B1a/B1b, were obtained.

Step B Preparation of 4''-Deoxy-4''-octylthio-avermectin B1a/B1b and 4''-Deoxy-4''-epi-octylthio-avermectin B1a/B1b The epimers, 4''-deoxy-4''-octylthio-5-O-tert.-butyldimethylsilyl-avermectin B1a/B1b and 4''-deoxy-4''-epi-octylthio-5-O-tert.-butyldimethylsilyl-avermectin B1a/B1b (123 mg, 0.110 mmol), obtained according to the procedures above, were dissolved in THF (4 mL). To this was added 2 mL of a HF-pyridine solution (25 g HF-pyridine, 10 mL pyridine, 28 mL THF). After 6 hours the reaction mixture was partitioned between water and ether. The aqueous layer was neutralized with a saturated solution of sodium bicarbonate and extracted with ethyl acetate. The combined ethyl acetate extracts were dried over magnesium sulfate, filtered, and concentrated. The crude product was purified by preparative thin layer silica gel chromatography using hexane-ethyl acetate (2:3) as eluant. Both epimeric products, 4''-deoxy-4''-octylthio-avermectin B1a/B1b and 4''-deoxy-4''-epi-octylthio-avermectin B1a/B1b were purified, separated and isolated. The products were characterized by nuclear magnetic resonance spectroscopy and mass spectroscopy (isomer A, (M+7)=1007; isomer B, (M+7)=1007), and purity was assessed by reversed-phase high pressure liquid chromatography.

Yield: epimer A, 41 mg; epimer B, 47 mg.

EXAMPLE 13

4''-Deoxy-4''-epi-thioacetyl-avermectin B1a/B1b

Step A Preparation of 4''-Deoxy-4''-epi-thioacetyl-5-O-tert.-butyldimethylsilyl-avermectin B1a/B1b A solution of 4''-O-trifluoromethanesulfonyl-5-O-tert.-butyldimethylsilyl-avermectin B1a/B1b (93 mg, 0.839 mmol) in DMF (2 mL) was cooled to 0° C. To the cooled solution was added potassium thioacetate (28 mg, 0.249 mmol). The reaction mixture was allowed to warm to room temperature over 1 hour. After 3 hours at room temperature, the reaction was quenched with water, and the product was extracted with methylene chloride. After drying over magnesium sulfate, the methylene chloride extract was concentrated in vacuo, and purified by preparative thin-layer silica gel chromatography using hexane-ethyl acetate (80:20). The pure product, 4'''-deoxy-4''-epi-thioacetyl-5-O-tert.-butyldimethylsilyl-avermectin B1a/B1b, was characterized by nuclear magnetic resonance spectroscopy and purity was assessed by reversed-phase high pressure liquid chromatography. Yield 54 mg, colorless glass.

Step B Preparation of 4''-Deoxy-4''-epi-thioacetyl-avermectin B1a/B1b

A solution of 4''-deoxy-4''-epi-thioacetyl-5-O-tert.-butyldimethylsilyl-avermectin B1a/B1b (54 mg, 0.051 mmol) was dissolved in THF, (2.5 mL). To this solution was added 1 mL of a HF-pyridine solution (25 g HF-pyridine, 10 mL pyridine, 28 mL THF), and the reaction mixture was stirred at room temperature. After 6 hours, the reaction mixture was cooled to 0° C., diluted with pyridine (3 mL), and quenched with 3 mL of a saturated sodium bicarbonate solution, plus sufficient solid sodium bicarbonate to neutralize the acid. The crude product was extracted with ethyl acetate, washed with brine, dried over magnesium sulfate, filtered, concentrated, and purified by preparative thin-layer silica gel chromatography using hexane-ethyl acetate (1:1). The pure product, 4''-deoxy-4''-epi-thioacetyl-avermectin B1a/B1b, was characterized by nuclear magnetic resonance spectroscopy and purity was assessed by reversed-phase high pressure liquid chromatography.

Yield, 42 mg of fluffy white powder.

EXAMPLE 14

4''-Deoxy-4''-epi-thio-avermectin B1a/B1b

A solution of 4''-deoxy-4''-epi-thioacetyl-avermectin B1a/B1b (21 mg, 0.023 mmol, prepared according to the procedure of Example 13) in methanol (1 mL) was cooled to 0° C., and 1 mL methanol saturated with ammonia was added. The reaction mixture was allowed to warm to room temperature. After 3 days, the reaction mixture was concentrated in vacuo and the crude product was purified by preparative thin-layer silica gel chromatography using hexane-ethyl acetate (1:1). The pure product, 4''-deoxy-4''-epi-thio-avermectin B1a/B1b, was characterized by high pressure liquid chromatography and nuclear magnetic resonance spectroscopy. Yield 16 mg.

EXAMPLE 15

4''-Deoxy-4''-thiocyanato-avermectin B1a/B1b and

4''-Deoxy-4''-epi-thiocyanato-avermectin B1a/B1b

To a solution of 4''-O-trifluoromethanesulfonyl-5-O-tert.-butyldimethylsilyl-avermectin B1a/B1b (125 mg, 0.112 mmol) in DMF (5 mL) was added tetrabutylammonium thiocyanate (192 mg, 0.640 mmol). After 2 hours, the reaction mixture was partitioned between water and ethyl acetate. The organic layer was dried over magnesium sulfate, filtered, and concentrated in vacuo. The crude epimeric products were then dissolved in THF (2 mL) at room temperature, to which solution was added 1 mL of an HF-pyridine solution (25 g HF-pyridine, 10 mL pyridine, 28 mL THF). After 16 hours, the reaction mixture was cooled to 0° C., diluted with pyridine (3 mL), quenched with a saturated sodium bicarbonate solution (25 mL), poured into a saturated sodium chloride solution (brine, 40 mL), extracted with methylene chloride, dried over magnesium sulfate, and concentrated in vacuo. The two epimeric products were separated and purified by preparative thin-layer silica gel chromatography using ethyl acetatemethylene chloride (15:85). The pure products, 4''-deoxy-4''-thiocyanato-avermectin B1a/B1b and 4''-deoxy-4''-epi-thiocyanato-avermectin B1a/B1b, were characterized by nuclear magnetic resonance spectroscopy and purity was assessed by reversed-phase high pressure liquid chromatography.

EXAMPLE 16

4''-Deoxy-4''-epi-iodo-avermectin B1a/B1b

Step A Preparation of 4''-Deoxy-4''-epi-iodo-5-O-tert.-butyldimethylsilyl-avermectin B1a/B1b To a stirring, room temperature solution of 4''-O-trifluoromethanesulfonyl-5-O-tert.-butyldimethylsilyl-avermectin B1a/B1b (125 mg, 0.111 mmol) in 1 mL DMF, was added potassium iodide (166 mg, 0.111 mmol). After 4 hours the reaction mixture was partitioned between a saturated sodium chloride solution and methylene chloride. The methylene chloride extract was dried over magnesium sulfate, and concentrated in vacuo. The crude product was filtered through a plug of silica gel using hexane-ethyl acetate (1:1), concentrated in vacuo, and further purified by preparative thin-layer silica gel chromatography using hexane-ethyl acetate (3:1).

Step B Preparation of 4''-Deoxy-4''-epi-iodo-avermectin B1a/B1b

4''-Deoxy-4''-epi-iodo-5-O-tert.-butyldimethylsilyl-avermectin B1a/B1b (100 mg, 0.102 mmol prepared above) is dissolved in tetrahydrofuran (THF, 2.5 mL). To this solution is added 1 mL of a HF-pyridine solution (25 g HF-pyridine, 10 mL pyridine, 28 mL THF), and the reaction mixture is stirred at room temperature. After 6 hours, the reaction mixture is cooled to 0° C., diluted with pyridine (3 mL), and quenched with 3 mL of a saturated sodium bicarbonate solution, plus sufficient solid sodium bicarbonate to neutralize the acid. The crude product is extracted with ethyl acetate, washed with brine, dried over magnesium sulfate, filtered, concentrated, and purified by preparative thin-layer silica gel chromatography using hexane-ethyl acetate (1:1). The pure product, 4''-deoxy-4''-epi-iodo-avermectin B1a/B1b, is characterized by nuclear magnetic resonance spectroscopy, and purity is assessed by reversed-phase high pressure liquid chromatography.

EXAMPLE 17

4''-Deoxy-4''-thioacetyl-avermectin B1a/B1b

Step A Preparation of 4''-Deoxy-4''-thioacetyl-5-O-tert.-butyldimethylsilyl-avermectin B1a/B1b 4''-Deoxy-4''-epi-iodo-5-O-tert.-butyldimethylsilyl-avermectin B1a/B1b (75 mg, 0.076 mmol, prepared according to Example 16, Step A) is added to a stirring, room-temperature solution of DMF (1 mL), 5 mg 18-crown-6 (1,4,7,10,13,16-hexaoxacyclooctadecane, 0.019 mmol), and potassium thioacetate (100 mg, 0.889 mmol). After 8 hours the reaction mixture is poured into 10 mL water, and extracted with ethyl acetate. The organic extract is dried over magnesium sulfate, filtered, concentrated in vacuo and purified by flash silica gel chromatography with hexane-ethyl acetate (4:1). The pure product, 4''-deoxy-4''-thioacetyl-5-O-tert.-butyldimethylsilyl-avermectin B1a/B1b, is characterized by nuclear magnetic resonance spectroscopy and purity is determined by high pressure liquid chromatography.

Step B Preparation of 4''-Deoxy-4''-thioacetyl-avermectin B1a/B1b

4''-Deoxy-4''-thioacetyl-5-O-tert.-butyldimethylsilyl-avermectin B1a/B1b is deprotected and purified according to the procedure in Example 13, Step B. The pure product, 4''-deoxy-4''-thioacetyl-avermectin B1a/B1b, is characterized by nuclear magnetic resonance spectroscopy, and purity is assessed by reversed-phase high pressure liquid chromatography.

EXAMPLE 18

4''-Deoxy-4''-epi-(2-hydroxyethyl)-thio-avermectin B1a/B1b

Step A Preparation of 4''-Deoxy-4''-epi-(2-hydroxyethyl)-thio-5-O-tert.-butyldimethylsilyl-avermectin B1a/B1b To a stirring, room-temperature solution of 4''-O-trifluoromethanesulfonyl-5-O-butyldimethylsilyl-avermectin B1a/B1b (100 mg, 0.089 mmol) in dimethylformamide (DMF, 2 mL) is added 5 mg 18-crown-6(1,4,7,10,13,16-hexaoxacyclooctadecane, 0.019 mmol) and 200 µL 2-mercaptoethanol (0.285 mmol), followed by potassium carbonate (62 mg, 0.447 mmol). After 3 hours, the reaction mixture is poured into 10 mL water and extracted with methylene chloride. The organic extract is washed with brine, dried over magnesium sulfate, concentrated in vacuo, and purified by flash silica gel chromatography using hexane-ethyl acetate (6:4). The product 4''-deoxy-4''-epi-(2-hydroxyethyl)-thio-5-O-tert.-butyldimethylsilyl-avermectin B1a/B1b is characterized by nuclear magnetic resonance spectroscopy.

Step B Preparation of 4''-Deoxy-4''-epi-(2-hydroxyethyl)-thio-avermectin B1a/B1b The product obtained above, 4''-deoxy-4''-epi-(2-hydroxyethyl)-thio-5-O-tert.-butyldimethylsilyl-avermectin B1a/B1b, is dissolved in THF (4 mL). To this is added 2 mL of a HF-pyridine solution (25 g HF-pyridine, 10 mL pyridine, 28 mL THF). After 6 hours the reaction mixture is partitioned between water and ether. The aqueous layer is neutralized with a saturated solution of sodium bicarbonate and extracted with ethyl acetate. The combined ethyl acetate extracts are dried over magnesium sulfate, filtered, and concentrated. The crude product is purified by preparative thin layer silica gel chromatography using hexane-ethyl acetate (2:3) as eluant. The pure product, 4''-deoxy-4''-epi-(2hydroxyethyl)-thio-avermectin B1a/B1b, is characterized by nuclear magnetic resonance spectroscopy, and purity is assessed by reversed-phase high pressure liquid chromatography.

EXAMPLE 19

4''-Deoxy-4''-epi-(2-acetoxyethyl)-thio-avermectin B1a/B1b

Step A Preparation of 4''-Deoxy-4''-epi-(2-acetoxyethyl)-thio-5-tert.-butyldimethylsilyl-avermectin B1a/B1b To a stirring solution of 4''-deoxy-4''-epi-(2-hydroxyethyl)-thio-5-O-tert.-butyl-dimethylsilyl-avermectin B1a/B1b (100 mg, 0.097 mmol, product of Example 18, Step A) in methylene chloride (2 mL) at 0° C. is added 100 µL pyridine, followed by 100 µL acetic anhydride and 5 mg 4-dimethylaminopyridine. The ice bath is removed and the reaction mixture is stirred at room temperature for 1 hour, then poured directly onto a silica gel flash chromatography column using hexane-ethyl acetate (3:1) as eluent. Fractions containing product are combined and concentrated in vacuo. The product 4''-deoxy-4''-epi-(2-acetoxyethyl)-thio-5-O-tert.- butyl-dimethylsilyl-avermectin B1a/B1b is characterized by nuclear magnetic resonance spectroscopy.

Step B Preparation of 4''-Deoxy-4''-epi-(2-acetoxyethyl)-thio-avermectin B1a/B1b The product obtained above, 4''-deoxy-4''-epi-(2-acetoxyethyl)-thio-5-O-tert.-butyldimethylsilyl-avermectin B1a/B1b, is dissolved in THF (4 mL). To this is added 2 mL of a HF-pyridine solution (25 g HF-pyridine, 10 mL pyridine, 28 mL THF). After 6 hours the reaction mixture is partitioned between water and ether. The aqueous layer is neutralized with a saturated solution of sodium bicarbonate and extracted with ethyl acetate. The combined ethyl acetate extracts are dried over magnesium sulfate, filtered, and concentrated. The crude product is purified by preparative thin layer silica gel chromatography using hexane-ethyl acetate (2:3) as eluant. The pure product, 4''-deoxy-4''-epi-(2-acetoxyethyl)-thio-avermectin B1a/B1b, is characterized by nuclear magnetic resonance spectroscopy, and purity is assessed by reversed-phase high pressure liquid chromatography.

EXAMPLE 20

4''-Deoxy-4''-epi-(2-aminoethyl)-thio-avermectin B1a/B1b

Step A Preparation of 4''-Deoxy-4''-epi-(2-aminoethyl)-thio-5-O-tert.-butyldimethylsilyl-avermectin B1a/B1b To a stirring solution of 4''-deoxy-4''-epi-(2-hydroxyethyl)-thio-5-O-tert.-butyl-dimethylsilyl-avermectin B1a/B1b (100 mg, 0.097 mmol, product of Example 18, Step A) in 3 mL THF at 0° C. is added 8 mg pyridine (0.097 mmol), followed by 18.5 mg tosyl chloride (0.097 mmol). After stirring for 1 hour at 0° C., ammonia gas is bubbled through the solution until the solution is saturated. The solution is allowed to warm to room temperature. After stirring for 2 hours, the reaction mixture is poured into 10 mL water and extracted with methylene chloride. The organic extract is washed with brine, dried over magnesium sulfate, concentrated in vacuo, and purified by flash silica gel chromatography using hexane-ethyl acetate (1:9). The product 4''-deoxy-4''-epi-(2-aminoethyl)-thio-5-O-tert.-butyldimethylsilyl-avermectin B1a/B1b is characterized by nuclear magnetic resonance spectroscopy.

Step B Preparation of 4''-Deoxy-4''-epi-(2-aminoethyl)-thio-avermectin B1a/B1b

The product obtained above, 4''-deoxy-4''-epi-(2-aminoethyl)-thio-5-O-tert.-butyldimethylsilyl-avermectin B1a/B1b, is dissolved in THF (4 mL). To this is added 2 mL of a HF-pyridine solution (25 g HF-pyridine, 10 mL pyridine, 28 mL THF). After 6 hours the reaction mixture is partitioned between water and ether. The aqueous layer is neutralized with a saturated solution of sodium bicarbonate and extracted with ethyl acetate. The combined ethyl acetate extracts are dried over magnesium sulfate, filtered, and concentrated. The crude product is purified by preparative thin layer silica gel chromatography using hexane-ethyl acetate (2:3) as eluant. The pure product, 4''-deoxy-4''-epi-(2-aminoethyl)-thio-avermectin B1a/B1b, is characterized by nuclear magnetic resonance spectroscopy, and purity is assessed by reversed-phase high pressure liquid chromatography.

EXAMPLE 21

4''-Deoxy-4''-epi-(2-(2-O-tetrahydropyranyl)ethylthio)-avermectin B1a/B1b

Step A Preparation of 4''-Deoxy-4''-epi-(2-(2-O-tetrahydropyranyl)-ethylthio)-5-O-tert.-butyldimethylsilyl-avermectin B1a/B1b To a stirring solution of 4''-deoxy-4''-epi-(2-hydroxyethyl)-thio-5-O-tert.-butyldimethylsiyl-avermectin B1a/B1b (100 mg, 0.097 mmol, product of Example 18, Step A) in 3 mL methylene chloride at 0° C. is added 100 μL 3,4-dihydro-2H-pyran, followed by 5 mg pyridinium p-toluenesulfonate. After stirring for 10 minutes at 0° C., the reaction mixture is allowed to warm to room temperature. After 30 minutes, 100 μL triethylamine is added, and the reaction mixture is concentrated in vacuo at ambient temperature. The product is purified by flash silica gel chromatography using hexane-ethyl acetate (3:1). The product, 4''-deoxy-4''-epi-(2-(2-O-tetrahydropyranyl)-ethylthio)-5-O-tert.-butyl-dimethylsilyl-avermectin B1a/B1b is characterized by nuclear magnetic resonance spectroscopy.

Step B Preparation of 4''-Deoxy-4''-epi-(2-(2-O-tetrahydropyranyl)-ethylthio)-avermectin B1a/B1b The product obtained above, 4''-deoxy-4''-epi-(2-(2-O-tetrahydropyranyl)-ethylthio)-5-O-tert.-butyldimethylsilyl-avermectin B1a/B1b, is dissolved in THF (4 mL). To this is added 2 mL of a HF-pyridine solution (25 g HF-pyridine, 10 mL pyridine, 28 mL THF). After 6 hours the reaction mixture is partitioned between water and ether. The aqueous layer is neutralized with a saturated solution of sodium bicarbonate and extracted with ethyl acetate. The combined ethyl acetate extracts are dried over magnesium sulfate, filtered, and concentrated. The crude product is purified by preparative thin layer silica gel chromatography using hexane-ethyl acetate (2:3) as eluant. The pure product, 4''-deoxy-4''-epi-(2-(2-O-tetrahydropyranyl)-ethylthio)-avermectin B1a/B1b, is characterized by nuclear magnetic resonance spectroscopy, and purity is assessed by reversed-phase high pressure liquid chromatography.

EXAMPLE 22

4''-Deoxy-4''-epi-thioacetyl-avermectin B2a/B2b

Step A Preparation of the Intermediate 4''-O-Trifluoromethanesulfonyl-5,23-bis-O-tert.-butyldimethylsilyl-avermectin B2a/B2b To a stirring solution of 5,23-bis-O-tert.-butyldimethylsilyl-avermectin B1a/B1b (500 mg, 454 mmol) in dry methylene chloride filtered through basic alumina (10.0 mL), N,N-diisopropylethylamine (0.620 mL, 3.56 mmol) is added followed by 4-dimethylaminopyridine (DMAP, 122 mg, 3.56 mmol). The solution is cooled to 0° C. under nitrogen, and trifluoromethanesulfonic anhydride (0.400 mL, 2.38 mmol) is added over 1 minute. After 1 hour at 0° C., the reaction mixture is partitioned between ice/water and methylene chloride. The methylene chloride extracts are dried over magnesium sulfate, filtered and concentrated in vacuo. The crude product is purified through a plug of silica gel using hexane-ethyl acetate (3:1). The product is concentrated to an oil and lyophilized from benzene. The pure product, 4''-O-trifluoromethanesulfonyl-5,23-bis-O-tert.-butyldimethylsilyl-avermectin B2a/B2b, is characterized by nuclear magnetic resonance spectroscopy.

Step B Preparation of 4''-Deoxy-4''-epi-thioacetyl-5,23-bis-O-tert.-butyldimethylsilyl-avermectin B2a/B2b 4''-O-Trifluoromethanesulfonyl-5,23-bis-O-tert.-butyldimethylsilyl-avermectin B2a/B2b (75 mg, 0.06 mmol) is added to a stirring, room temperature solution of in 1 mL DMF, 5 mg 18-crown-6 (1,4,7,10,13,16-hexaoxacyclooctadecane, 0.019 mmol), and potassium thioacetate (100 mg, 0.889 mmol). After 8 hours the reaction mixture is poured into 10 mL water, and extracted with ethyl acetate. The organic extract is dried over magnesium sulfate, filtered, concentrated in vacuo and purified by flash silica gel chromatography with hexane-ethyl acetate (4:1). The pure product, 4''-deoxy-4''-epi-thioacetyl-5,23-bis-O-tert.-butyldimethylsilyl-avermectin B2a/B2b, is characterized by nuclear magnetic resonance spectroscopy, and purity is assessed by reversed-phase high pressure liquid chromatography.

Step C Preparation of 4''-deoxy-4''-epi-thioacetyl-avermectin B2a/B2b

4''-Deoxy-4''-epi-thioacetyl-5,23-bis-O-tert.-butyldimethylsilyl-avermectin B2a/B2b is deprotected and purified according to the procedure in Example 13, Step B. The pure product, 4''-deoxy-4''-epi-thioacetyl-avermectin B2a/B2b, is characterized by reversed-phase high pressure liquid chromatography and nuclear magnetic resonance spectroscopy.

EXAMPLE 23

4'-Deoxy-4'-epi-methylthio-avermectin B1a/B1b monosaccharide

Step A Preparation of the Intermediate 4'-O-Trifluoromethanesulfonyl-5-O-tert.-butyldimethylsilyl-avermectin B1a/B1b monosaccharide To a stirring solution of 5-O-tert.-butyldimethylsilyl-avermectin B1a/B1b monosaccharide (500 mg, 0.593 mmol) in dry methylene chloride (30.0 mL), N,N-diisopropylethlyamine (0.620 μL, 3.56 mmol) was added followed by 4-dimethylaminopyridine (DMAP, 435 mg, 3.56 mmol). The solution was cooled to 0° C. under nitrogen, and trifluoromethanesulfonic anhydride (4.097 mL, 2.38 mmol) was added over 1 minute. After 1 hour at 0° C., the reaction mixture was partitioned between ice/water and methylene chloride. The methylene chloride extracts were dried over magnesium sulfate, filtered and concentrated in vacuo. The crude product was purified through a 2'' plug of silica gel using hexane-ethyl acetate (3:1). The product was concentrated to an oil and lyophilized from benzene. the pure product, 4'-deoxy-4'-trifluoromethanesulfonyl-5-O-tert.-butyldimethylsilyl-avermectin B1a/B1b monosaccharide, was characterized by nuclear magnetic resonance spectroscopy. Yield 495 mg of a light tan solid.

Step B Preparation of 4'-Deoxy-4'-epi-methylthio-5-O-tert.-butyldimethylsilyl-avermectin B1a/B1b monosaccharide Gaseous methane thiol is bubbled moderately fast through dry dimethylformamide 4 mL) for 2.0 minutes, followed by the addition of potassium carbonate (231 mg, 1.671 mmol). After the solution is cooled to 0° C. under nitrogen, 4'-O-trifluoromethanesulfonyl-5-O-tert.-butyldimethylsilyl-avermectin B1a/B1b monosaccharide (1244 mg, 1.11 mmol), prepared according to the procedures above, is added. After 20 minutes, the reaction mixture is allowed to warm to room temperature. After stirring at room temperature for an additional 2 hours, the reaction mixture is partitioned between a solution of saturated sodium bicarbonate and methylene chloride. The methylene chloride extracts are washed with water, dried over magnesium sulfate, filtered, and concentrated to an oil. The crude product is purified by flash silica gel column chromatography using hexane-ethyl acetate (3:1). The fractions containing product were pooled, and the pure product, 4'-deoxy-4'-epi-methylthio-5-O-tert.-butyldimethylsilyl-avermectin B1a/B1b monosaccharide, is characterized by nuclear magnetic resonance spectroscopy, and purity is assessed by reversed-phase high pressure liquid chromatography.

Step C Preparation of 4'-deoxy-4'-epi-methylthio-avermectin B1a/B1b monosaccharide 4'-Deoxy-4'-epi-methylthio-5-O-tert.-butyldimethylsilyl-avermectin B1a/B1b monosaccharide (284 mg, 0.325 mmol), prepared according to the procedures above, is dissolved in 4 mL THF. To this is added 2 mL of a HF-pyridine solution (25 g HF-pyridine, 10 mL pyridine, 28 mL THF). After 5 hours, the reaction mixture is cooled to 0° C., diluted with ether (2 mL), and poured into cold water (15–20 mL). Additional ether is added. The aqueous layer is removed, and the organic layer is washed with a saturated aqueous sodium bicarbonate solution (5–10 mL), which is added to the water extract. Additional sodium bicarbonate is added to the combined aqueous washings until foaming ceases. The aqueous layer is then extracted with ether, and all ether extracts are combined, washed with water, dried over magnesium sulfate, filtered, and concentrated to a yellow oil. The crude product is purified by flash silica gel chromatography using hexane-ethyl acetate (60:40). The fractions containing product are pooled, concentrated in vacuo, and lyophilized from benzene. The pure product, 4''-deoxy-4''-epi-methylthio-avermectin B1a/B1b monosaccharide is characterized by nuclear magnetic resonance spectroscopy, and purity is determined by reversed-phase high pressure liquid chromatography.

EXAMPLE 24

4'-Deoxy-4'-octylthio-avermectin B1a/B1b monosaccharide and
4'-Deoxy-4'-epi-octylthio-avermectin B1a/B1b monosaccharide Step A Preparation of 4'-Deoxy-4'-octylthio-5-O-tert.-butyldimethylsilyl-avermectin B1a/B1b monosaccharide and 4'-Deoxy-4'-epi-octylthio-5-O-tert.-butyldimethylsilyl-avermectin B1a/B1b monosaccharide To a stirring, room-temperature solution of 4'-O-trifluoromethylsulfonyl-5-O-tert.-butyldimethylsilyl-avermectin B1a/B1b monosaccharide (105 mg, 0.107 mmol) in dimethylformamide (DMF, 1 mL) was added n-octyl mercaptan (79 μL, 0.539 mmol) and potassium carbonate (74 mg, 0.539 mmol). After 2.5 hours, the reaction mixture was partitioned between a saturated solution of sodium bicarbonate and ethyl acetate. The ethyl acetate extract was dried over magnesium sulfate, concentrated in vacuo, and purified by preparative thin-layer silica gel chromatography using hexane-ethyl acetate (85:15). Both epimeric products, 4'-deoxy-4'-octylthio-5-O-tert.-butyldimethylsilyl-avermectin B1a/B1b monosaccharide and 4'-deoxy-4'-epi-octylthio-5-O-tert.-butyldimethylsilyl-avermectin B1a/B1b monosaccharide, were separated and isolated.

Step B Preparation of 4'-Deoxy-4'-octylthio-avermectin B1a/B1b monosaccharide

A solution of 4'-deoxy-4'-octylthio-5-O-tert.-butyldimethylsilyl-avermectin B1a/B1b monosaccharide (obtained in Step A) was dissolved in 2 mL THF. To this solution was added 1 mL of a HF-pyridine solution (25 g HF-pyridine, 10 mL pyridine, 28 mL THF), and the reaction mixture was stirred at room temperature. After 12 hours, the reaction mixture was cooled to 0° C., diluted with pyridine (3 mL), and quenched with 3 mL of a saturated sodium bicarbonate solution, plus sufficient solid sodium bicarbonate to neutralize the acid. The crude product was extracted with ethyl acetate, washed with brine, dried over magnesium sulfate, filtered, concentrated, and purified by preparative thin-layer silica gel chromatography using hexane-ethyl acetate (1:1). The pure product, 4'-deoxy-4'-octylthio-avermectin B1a/B1b monosaccharide, was characterized by nuclear magnetic resonance spectroscopy, and purity was assessed by reversed-phase high pressure liquid chromatography.

Step C Preparation of 4'-Deoxy-4'-epi-octylthio-avermectin B1a/B1b monosaccharide A solution of 4'-deoxy-4'-epi-octylthio-5-O-tert.-butyldimethylsilyl-avermectin B1a/B1b monosaccharide (obtained in Step A) was dissolved in 2 mL THF. To this solution was added 1 mL of a HF-pyridine solution (25 g HF-pyridine, 10 mL pyridine, 28 mL THF), and the reaction mixture was stirred at room temperature. After 12 hours, the reaction mixture was cooled to 0° C., diluted with pyridine (3 mL), and quenched with 3 mL of a saturated sodium bicarbonate solution, plus sufficient solid sodium bicarbonate to neutralize the acid. The crude product was extracted with ethyl acetate, washed with brine, dried over magnesium sulfate, filtered, concentrated, and purified by preparative thin-layer silica gel chromatography using hexane-ethyl acetate (1:1). The pure product, 4'-deoxy-4'-epi-octylthio-avermectin B1a/B1b monosaccharide, was characterized by nuclear magnetic resonance spectroscopy, and purity was assessed by reversed-phase high pressure liquid chromatography.

EXAMPLE 25

4'-Deoxy-4'-epi-thioacetyl-avermectin B1a/B1b monosaccharide

Step A Preparation of 4'-Deoxy-4'-epi-thioacetyl-5-O-tert.-butyldimethylsilyl-avermectin B1a/B1b monosaccharide A solution of 4'-O-trifluoromethanesulfonyl-5-O-tert.-butyldimethylsilyl-avermectin B1a/B1b monosaccharide (125 mg, 0.128 mmol) in dimethylformamide (DMF, 2 mL) was cooled to 0° C. To the cooled solution was added potassium thioacetate (44 mg, 0.385 mmol). The reaction mixture was allowed to warm to room temperature over 1 hour. After 3 hours at room temperature, the reaction mixture was partitioned between water and methylene chloride. After drying over magnesium sulfate, the methylene chloride extract was concentrated in vacuo, and purified by preparative thin-layer silica gel chromatography using hexane-ethyl acetate (85:15). The pure product, 4'-deoxy-4'-epi-thioacetyl-5-O-tert.-butyldimethylsilyl-avermectin B1a/B1b monosaccharide was characterized by nuclear magnetic resonance spectroscopy, and purity was assessed by reversed-phase high pressure liquid chromatography.

Step B Preparation of 4'-Deoxy-4'-epi-thioacetyl-avermectin B1a/B1b monosaccharide A solution of 4'-deoxy-4'-epi-thioacetyl-5-O-tert.-butyldimethylsilyl-avermectin B1a/B1b monosaccharide (64 mg, 0.071 mmol) in tetrahydrofuran (THF, 2.5 mL) was treated with 1 mL HF-pyridine solution (25 g HF-pyridine, 10 mL pyridine, 28 mL THF) at room temperature. After 6 hours, the reaction mixture was cooled to 0° C., diluted with 3 mL pyridine, quenched with 3 mL aqueous saturated sodium bicarbonate solution plus sufficient solid sodium bicarbonate to neutralize the acid. The product was extracted with ethyl acetate, washed with brine, dried over magnesium sulfate, filtered, and concentrated. The crude product was purified by preparative thin-layer silica gel chromatography using hexane-ethyl acetate (1:1). Pure 4'-deoxy-4'-epi-thioacetyl-avermectin B1a/B1b monosaccharide was characterized by nuclear magnetic resonance spectroscopy and purity was assessed by reversed-phase high pressure liquid chromatography. Yield 42 mg fluffy white powder.

EXAMPLE 26

4'-Deoxy-4'-epi-thio-avermectin B1a/B1b monosaccharide

Step A Preparation of 4'-Deoxy-4'-epi-thio-avermectin B1a/B1b monosaccharide

A solution of 4'-deoxy-4'-epi-thioacetyl-avermectin B1a/B1b (21 mg, 0.027 mmol) in methanol (1 mL) was cooled to 0° C., and 1 mL methanol saturated with ammonia was added. The reaction mixture was allowed to warm to room temperature. After 3 days, the reaction mixture was concentrated in vacuo and the crude product was purified by preparative thin-layer silica gel chromatography using hexane-ethyl acetate (1:1). Pure 4'-deoxy-4'-epi-thio-avermectin B1a/B1b monosaccharide was characterized by nuclear magnetic resonance spectroscopy, and mass spectroscopy, (M+7)=751. Purity was assessed by reversed-phase high pressure liquid chromatography.

EXAMPLE 27

4'-Deoxy-4'-thiocyanato-avermectin B1a/B1b monosaccharide and
4'-Deoxy-4'-epi-thiocyanato-avermectin B1a/B1b monosaccharide Step A Preparation of 4'-Deoxy-4'-thiocyanato-5-O-tert.-butyldimethylsilyl-avermectin B1a/B1b monosaccharide and 4'-deoxy-4'-epi-thiocyanato-5-O-tert.-butyldimethylsilyl-avermectin B1a/B1b monosaccharide and 4'-deoxy-4'-thiocyanato-5-O-tert.-butyldimethylsilyl-avermectin B1a/B1a To a solution of 4'-O-trifluoromethanesulfonyl-5-O-tert.-butyldimethylsilyl-avermectin B1a/B1b (125 mg, 0.128 mmol) in dimethylformamide (DMF, 1.0 mL) was added tetrabutylammonium thiocyanate (192 mg, 0.640 mmol). After 2 hours, the reaction mixture was partitioned between water and ethyl acetate. The organic layer was dried over magnesium sulfate, filtered, and concentrated in vacuo. The two epimeric products were separated and purified by preparative thin-layer silica gel chromatography using hexane-ethyl acetate (3:1).

The mixture of products, 4'-deoxy-4'-epi-thiocyanato-5-O-tert.-butyldimethylsilyl-avermectin B1a/B1b, and 4'-deoxy-4'-thiocyanato-5-O-tert. butyldimethylsilyl-avermectin B1a/B1b were deprotected as detailed below.

Step B Preparation of 4'-Deoxy-4'-thiocyanato-avermectin B1a/B1b monosaccharide and 4'-Deoxy-4'-epi-thiocyanato-avermectin B1a/B1b monosaccharide To a room temperature solution of 4'-deoxy-4'-thiocyanato-5-O-tert.-butyldimethylsilyl-avermectin B1a/B1b monosaccharide and 4'-deoxy-4'-thiocyanato- 5-O-tert.-butyldimethylsilyl-avermectin B1a/B1b monosaccharide (product of Step A) in 2 mL THF, was added 1 mL of an HF-pyridine solution (25 g HF-pyridine, 10 mL pyridine, 28 mL THF). After 16 hours, the reaction mixture was cooled to 0° C., diluted with pyridine (3 mL), quenched with a saturated sodium bicarbonate solution (25 mL), poured into a saturated sodium chloride solution (brine, 40 mL), extracted with methylene chloride, dried over magnesium sulfate, and concentrated in vacuo. The two epimeric products were separated and purified by preparative thin-layer silica gel chromatography using ethyl acetate-methylene chloride (10:90). The pure products, 4'-deoxy-4'-thiocyanato-avermectin B1a/B1b monosaccharide and 4'-deoxy-4'-epi-thiocyanato-avermectin B1a/B1b monosaccharide, were characterized by nuclear magnetic resonance spectroscopy and mass spectroscopy (isomer A, (M+7)=776, isomer B, (M+7)=776. Purity was assessed by reversed-phase high pressure liquid chromatography.

EXAMPLE 28

4'-Deoxy-4'-epi-[3-thio-(methylproprionate)]-avermectin B1a/B1b monosaccharide

Step A Preparation of 4'-Deoxy-4'-epi-[3-thio-(methylproprionate)]-5-O-tert.-butyldimethylsilyl-avermectin B1a/B1b monosaccharide To a stirring, room-temperature solution of 4'-O-trifluoromethanesulfonyl-5-O-tert.-butyldimethylsilyl-avermectin B1a/B1b monosaccharide (100 mg, 0.103 mmol) in dimethylformamide (DMF, 1 mL) was added methyl 3-mercaptoproprionate (0.050 mL, 0.452 mmol) and potassium carbonate (30 mg, 0.217 mmol). After 3 hours, the reaction mixture was partitioned between a saturated sodium chloride solution and methylene chloride. The methylene chloride extract was dried over magnesium sulfate, filtered, concentrated in vacuo, and purified by preparative thin-layer silica gel chromatography using hexane-ethyl acetate (75:25). The pure product, 4'-deoxy-4'-epi-[3-thio-(methylproprionate)]-5-O-tert.-butyldimethylsilyl-avermectin B1a/B1b monosaccharide, was characterized by nuclear magnetic resonance spectroscopy, and purity was assessed by reversed-phase high pressure liquid chromatography.

Step B Preparation of 4'-Deoxy-4'-epi-[3-thio-(methylproprionate)]-avermectin B1a/B1b monosaccharide To a room-temperature solution of 4'-deoxy-4'-epi-[3-thio-(methylproprionate)]-5-O-tert.-butyldimethylsilyl-avermectin B1a/B1b monosaccharide obtained in Step A in 2 mL THF, was added 1 mL of an HF-pyridine solution (25 g HF-pyridine, 10 mL pyridine, 28 mL THF). After 6 hours, the reaction mixture was cooled to 0° C., diluted with pyridine (3 mL), quenched with a saturated sodium bicarbonate solution (25 mL), poured into a saturated sodium chloride solution (40 mL), extracted with methylene chloride, dried over magnesium sulfate, concentrated in vacuo, and purified by preparative thin-layer silica gel chromatography using ethyl acetate-methylene chloride (1:1). Pure 4'-deoxy-4'-epi-[3-thio-(methylproprionate)]-avermectin B1a/B1b monosaccharide was characterized by and nuclear magnetic resonance spectroscopy, and purity was assessed by reversed-phase high pressure liquid chromatography.

EXAMPLE 29

4''-Deoxy-4''-epi-methylthio-24-desmethyl-25-des-(2-butyl)-25-phenyl-avermectin B1.

Step A Preparation of 5-O-tert.-butyldimethylsilyl-24-desmethyl-25-des-(2-butyl)-25-phenyl-avermectin B1.

Starting with 24-desmethyl-25-des-(2-butyl)-25-phenyl-avermectin B1, obtained from Preparation T, 5-O-tert.-butyl-dimethylsilyl-24-desmethyl-25-des-(2-butyl)-25-phenyl-avermectin B1 is obtained employing the procedures of Preparation A.

Step B Preparation of 4''-deoxy-4''-epi-methylthio-24-desmethyl-25-des-(2-butyl)-25-phenyl-avermectin B1.

Starting with the product of Step A, the title compound is obtained employing the procedures of Example 1. The product is characterized by its NMR and mass spectra.

EXAMPLE 30

4''-Deoxy-4''-epi-methylthio-24-desmethyl-25-des-(2-butyl)-25-cyclopentyl-avermectin B1 and 4''-deoxy-4''-epi-methylthio-24-desmethyl-25-des-(2-butyl)-25-epi-cyclopentyl-avermectin B1

Starting with the products of Preparation U, the title compounds are prepared employing the procedures of Example 29, and are characterized by their mass and NMR spectra.

EXAMPLE 31

4''-Deoxy-4''-epi-methylthio-24-desmethyl-25-des-(2-butyl)-25-cyclohexyl-avermectin B1a and 4''-deoxy-4''-epi-methylthio-24-desmethyl-25-des-(2-butyl)-25-epi-cyclohexyl-avermectin B1a Starting with the products of Preparation V, the title compounds are prepared employing the procedures of Example 29, and are characterized by their mass and NMR spectra.

EXAMPLE 32

4''-Deoxy-4''-methylthio-25-des-(2-butyl)-25-alkyl-(aryl)-avermectin B1a and

4''-Deoxy-4''-methylthio-25-des-(2-butyl)-25-epi-alkyl-(aryl)-avermectin B1

Starting with the products of Preparation BB, the employing the procedures of Example 29, the following products are obtained:

4''-deoxy-4''-methylthio-25-des-(2-butyl)-25-(4-methoxyphenyl)-avermectin B1a;

4''-deoxy-4''-methylthio-25-des-(2-butyl)-25-(3,5-dichlorophenyl)-avermectin B1a;

4''-deoxy-4''-methylthio-25-des-(2-butyl)-25-(4-acetylaminophenyl)-avermectin B1a;

4''-deoxy-4''-methylthio-25-des-(2-butyl)-25-benzyl-avermectin B1a;

4''-deoxy-4''-methylthio-25-des-(2-butyl)-25-phenyl-avermectin B1a;

4''-deoxy-4''-methylthio-25-des-(2-butyl)-25-methyl-avermectin B1a;

4''-deoxy-4''-methylthio-25-des-(2-butyl)-25-ethyl-avermectin B1a; and their corresponding C-25 epimers, which are characterized by their NMR and mass spectra.

EXAMPLE 33

4"-Deoxy-4"-epi-methylthio-24-desmethyl-25-des-(2-butyl)-25-heterocyclo-avermectin B1a Starting with the following compounds from Preparation CC:
24-desmethyl-25-des-(2-butyl)-25-(3-furyl)-avermectin B1a;
24-desmethyl-25-des-(2-butyl)-25-(2-thienyl)-avermectin B1a; and
24-desmethyl-25-des-(2-butyl)-25-(4-pyridyl)-avermectin B1a;
the compounds below are synthesized using the procedures of Example 29.
4"-Deoxy-4"-epi-methylthio-24-desmethyl-25-des-(2-butyl)-25-(3-furyl)-avermectin B1a;
4"-Deoxy-4"-epi-methylthio-24-desmethyl-25-des-(2-butyl)-25-(2-thienyl)-avermectin B1a; and
4"-Deoxy-4"-epi-methylthio-24-desmethyl-25-des-(2-butyl)-25-(4-pyridyl)-avermectin B1a, are purified by high pressure liquid chromatography and characterized by their NMR and mass spectra.

EXAMPLE 34

4"-Deoxy-4"-epi-trifluoromethylthio-avermectin B1a/B1b

4"-Deoxy-4"-epi-thio-avermectin B1a/B1b (100 mg, 0.112 mmol, prepared according to Example 14) is placed in dimethylformamide (2 mL) at room temperature. To this is added anhydrous potassium carbonate (100 mg, 0.724 mmol), 18-crown-6 (5 mg) and trifluoromethyl iodide (300 mg, 1.53 mmol). The reaction is stirred at room temperature for 12 hours and is then poured into saturated brine (30 mL), extracted with methylene chloride and the organic layer is dried with magnesium sulfate. The solution is filtered and the solvent is removed in vacuo. The crude product is purified by silica gel chromatography to yield 4"-deoxy-4"-epi-trifluoromethylthio-avermectin B1a/B1b, which is characterized by 1H NMR and mass spectra.

EXAMPLE 35

4"-Deoxy-4"-epi-2,2,2-trifluoroethylthio-avermectin B1a/B1b

4"-Deoxy-4"-epi-thio-avermectin B1a/B1b (100 mg, 0.112 mmol, prepared according to Example 14) is placed in dimethylformamide (2 mL) at room temperature. To this is added anhydrous potassium carbonate (100 mg, 0,724 mmol), 18-crown-6 (5 mg) and 2,2,2-trifluoroethyl iodide (300 mg, 1.53 mmol). The reaction is stirred at room temperature for 12 hours and is then poured into saturated brine (30 mL), extracted with methylene chloride and the organic layer is dried with magnesium sulfate. The solution is filtered and the solvent is removed in vacuo. The crude product is purified by silica gel chromatography to yield 4"-deoxy-4"-epi-2,2,2-trifluoroethylthio-avermectin B1a/B1b, which is characterized by 1H NMR and mass spectra.

PREPARATION A.

5-O-tert.-Butyldimethylsilylavermectin B1a/B1b.

A solution of 50 g avermectin B1a/B1b (dried over $P_2O_5$ in high vacuum to constant weight), 24 g imidazole and 24 g tert.-butyldimethylsilyl chloride in 400 mL anhydrous dimethylformamide was stirred at room temperature for 50 minutes. The reaction mixture was poured into 1.5 L ice cold water and the aqueous phase was extracted four times with 200 mL ether. The organic phase was washed twice with water, aqueous sodium chloride solution, dried with magnesium sulfate, filtered and concentrated in vacuo to a white foam. The crude product was purified by silica gel column chromatography with a methylene chloride-ethyl acetate (90:10 to 70:30) solvent system to give 46.5 g 5-O-tert.-butyldimethylsilyl-avermectin B1a/B1b as an amorphous foam, which was characterized by its 1H-NMR and mass spectroscopy.

PREPARATION B.

5-O-tert.-Butyldimethylsilyl-4"-keto-avermectin B1a/B1b.

To a solution containing 9.1 mL oxalyl chloride in 230 mL dry methylene chloride stirred at −60° C. was added 15 mL dry dimethylsulfoxide over 15 minutes. Then a solution of 46.5 g 5-O-tert.-butyldimethylsilyl avermectin B1a/B1b dissolved in 230 mL dry methylene chloride was added over a period of 15 minutes while maintaining the temperature at −60° C. The reaction mixture was stirred at this temperature for 30 minutes when 65 mL dry triethylamine was added. The mixture was stirred for 5 additional minutes at −60° C., and then the cooling bath was removed and the reaction mixture was allowed to come to ambient temperature. After addition of water the reaction product was extracted with methylene chloride. The extract was washed with water, dried and concentrated in vacuo to 45.5 g of a yellow foam. This was identified by its mass and NMR spectra as 5-O-tert.-butyldimethylsilyl-4"-keto-avermectin B1a/B1b, which was used for further chemical reactions without purification.

PREPARATION C.

5-O-tert.-Butyldimethylsilyl-4"-epi-avermectin B1a/B1b

To a stirring solution of 10 g 5-O-tert.-butyldimethylsilyl-4"-keto-avermectin B1a/B1b (10.2 mM, obtained from prepartion B) in 50 mL methanol was added 386 mg sodium borohydride (10.2 mmol). After 15 minutes, 20 mL of a saturated aqueous solution of ammonium chloride was added. The reaction mixture was diluted with brine (20 mL), and extracted with ethyl acetate. The organic extracts were dried over magnesium sulfate, filtered, and concentrated in vacuo. The crude product was purified by silica gel column chromatography using hexane-ethyl acetate 13:1) to give 6.7 g 5-O-tert.-butyldimethylsilyl-4"-epi-avermectin B1a/B1b which was characterized by its 1H-NMR and mass spectroscopy.

PREPARATION D.

22,23-Dihydro-4"-keto-5-O-tert.-butyldimethylsilyl-avermectin B1a/B1b

To a solution of 97 μL oxalyl chloride in 2.5 mL methylene chloride stirred at −60° C. a solution of 160 μL dimethylsulfoxide in 1.0 mL methylene chloride was added dropwise over 3 minutes from a syringe. Then a solution of 500 mg 22,23-dihydro-5-O-tert.-butyldimethylsilyl-avermectin B1a/B1b in 3.0 mL of methylene chloride was added by syringe dropwise over 5 minutes. The reaction mixture was stirred at −60° C., for 30 minutes, when 0.71 mL triethylamine was added dropwise. After another 5 minutes at −60° C., the cooling bath was removed, and the reaction mixture was allowed to come to room temperature. Addition to water, extraction with ether, washing with water, drying and concentration in vacuo gave 520 mg of a yellow foam, which was purified by preparative silica gel thin layer chromatography with a methylene chloride-ethyl acetate (9:1) solvent mixture to give 470 mg pure 22,23-dihydro-4''-keto-5-O-tert.-butyldimethylsilyl-avermectin B1a/B1b, which was characterized by its mass and 300 mHz 1H-NMR spectra.

PREPARATION E.

22,23-Dihydro-4''-epi-5-O-tert.-butyldimethylsilyl-avermectin B1a/B1b

Starting with 22,23-dihydro-4''-keto-5-O-tert.-butyldimethylsilyl-avermectin B1a/B1b obtained in Preparation D, this product is prepared according to the methods of Preparation C.

PREPARATION F.

Avermectin B1a/B1b monosaccharide.

Avermectin B1a/B1b, 6.0 g, was dissolved in a stirred solution of iso-propanol containing 1.5 mL of conc. sulfuric acid at room temperature. After 41 hours the solution was concentrated under reduced pressure to 75 mL and then diluted with 25 mL water and 75 mL ethyl acetate. The mixture was neutralized with 50% aqueous sodium hydroxide and the layers were separated. The aqueous solution was extracted with ethyl acetate. The ethyl acetate solutions were combined, extracted with water, dried over sodium sulfate and evaporated under reduced pressure. Flash chromatography of the residue using hexane-acetone (3:1) furnished 3.1 g avermectin B1a/B1b monosaccharide which was characterized by nuclear magnetic resonance, mass spectra [735 (M+Li)] and high pressure liquid chromatographic analyses.

PREPARATION G.

5-O-tert.-Butyldimethylsilyl-avermectin B1a/B1b monosaccharide.

Avermectin B1a/B1b monosaccharide, 2.51 g, is treated with 1.44 g of imidazole and 1.44 g of tert.-butyldimethylsilyl chloride in 25 ml of anhydrous dimethylformamide by the procedure of Preparation A, furnishing 5-O-tert.-butyldimethylsilyl avermectin B1a/B1b monosaccharide.

PREPARATION H.

5-O-tert.-Butyldimethylsilyl-4'-oxoavermectin B1a/B1b monosaccharide

5-O-tert.-Butyldimethylsilyl-avermectin B1a/B1b monosaccharide, 2.1 g, is treated with of 0.49 mL oxalyl chloride and 0.81 mL dimethylsulfoxide in methylene chloride solution at −60° C. by the procedure of Preparation B furnishing 5-O-tert.-butyldimethylsilyl-4'-oxoavermectin B1a/B1b monosaccharide.

PREPARATION I.

4'',5-Di-O-t-Butyldimethylsilyl-Avermectin B2a.

To a solution of 58.2 g (65 mmol) of dried avermectin B2a in 400 mL of sieve-dried dimethylformamide and 30 mL of freshly distilled triethylamine was added a solution of 29.8 g (198 mmol, 3 equiv.) of t-butyldimethylsilyl chloride in 200 mL of dichloromethane. The mixture was stirred at room temperature 16 hours then poured into ice water and extracted with dichloromethane. The organic phases were combined and washed with water, brine, and dried over magnesium sulfate. Evaporation of the solvent afforded an oil which was purified by silica gel high performance liquid chromatography using 20% ethyl acetate-hexane to yield 34.2 g of 4'',5-Di-O-t-butyldimethylsilyl-avermectin B2a characterized by its NMR and mass spectra.

PREPARATION J.

4'',5-Di-O-t-Butyldimethylsilyl-23-oxo-Avermectin B2a.

A 5-L 3-neck flask equipped with a thermometer, mechanical stirrer, and dropping funnel was charged with 400 mL of dichloromethane and 16 mL (0.185 mol) of oxalyl chloride. The solution was cooled to −70° C., under nitrogen while a solution of 25 mL (0.350 mol) of dimethylsulfoxide in 200 mL of dichloromethane was added dropwise over 30 minutes keeping the internal temperature below −65° C. The mixture was stirred at −70° C. for 1 hour. A solution of 114.75 g (0.103 mol) of 4'',5-di-O-t-butyldimethylsilyl-avermectin B2a in 900 mL of dichloromethane was then added dropwise over 45 minutes keeping the temperature of the mixture below −65° C. After an additional 2 hours at −70° C., 115 mL of triethylamine was added dropwise over 10 minutes again keeping the temperature below −65° C. The reaction was then stirred at approximately 10° C. for 1 hour before the reaction mixture was concentrated in vacuo. The residue was taken up in 1.5 L ether and washed with 500 mL water. The aqueous layer was extracted with 500 mL ether. The combined ether layers were washed sequentially with 2×1 L of water, 1 L of saturated sodium bicarbonate, and 1 L of brine, then dried over magnesium sulfate. The solvent was removed to afford 110 g of yellow foam purified by column chromatography (4 kg silica gel, eluted with 5-25% ethyl acetate-hexane eluant). The product was obtained as a yellow foam (101 g, 88% yield), and was characterized by its NMR and Mass spectra.

PREPARATION K.

4'',5-Di-O-t-Butyldimethylsilyl-7-O-trimethylsilyl-O-23-trimethylsilyloxy-Avermectin B1a.

To a solution of 101 mg (0.09 mmol) of 4'',5-di-O-butyldimethylsilyl-23-oxo-avermectin B2a in 2 mL distilled tetrahydrofuran at −78° C. was added 0.400 mL of a 1.0M solution of lithium bis(trimethylsilyl)amide in a mixture of hexanes. The mixture was stirred at −78° C., under argon, for 1 hour before 0.20 mL of the supernatant of a centrifuged 1:3 mixture of triethylamine and trimethylchlorosilane was added dropwise by syringe. After another 30 minutes, 2 ml of a saturated aqueous sodium bicarbonate solution was added and a mixture was allowed to warm to room temperature. The reaction mixture was then partioned between water and ether and the ethereal extracts were combine and dried over magnesium sulfate. Filtration and evaporation of the ether afforded 120 mg of 4'',5-di-O-t-butyldimethylsilyl-7-O-trimethylsilyl-23-O-trimethylsiloxy-avermectin B1a characterized by its NMR and mass spectra.

PREPARATION L.

4'',5-Di-O-t-Butyldimethylsilyl-7-O-Trimethylsilyl-22-Hydroxy-23-Oxo-Avermectin B1a.

To a solution of 135 mg (0.107 mmol) of 4'',-5-Di-O-t-butyldimethylsilyl-7-O-trimethylsilyl-23-O-trimethylsilyl-Avermectin B1a in 2 mL of dichloromethane was added a solution of 21 mg (0.12 mmol) of m-chloroperbenzoic acid in 1 mL of dichloromethane in one portion. After 20 minutes at 20° C., 0.2 mL of dimethyl sulfide was added to react with any peracid. The mixture was stirred another 30 minutes before the addition of aqueous sodium bicarbonate and extraction with ethyl acetate. The combined organic fractions were dried, filtered, and evaporated to afford 150 mg of solid. This product mixture was separated by preparative thin layer chromatography (20% ethyl acetate-hexane) to afford 40 mg of 4'',5-Di-O-t-butyldimethylsilyl-7-O-trimethylsilyl-22-hydroxy-23-oxo-Avermectin B1a characterized by its NMR and mass spectra.

PREPARATION M.

Preparation of aldehyde-acid (Compound VI, Scheme 1).

To a solution of 600 mg (0.5 mmol) of 4",5-di-O-t-butyldimethylsilyl-7-O-trimethylsilyl-22-hydroxy-23-oxo-Avermectin B2a in 6 mL of benzene in an aluminum foil-covered glass vial was added 400 mg (0.9 mmol) lead tetraacetate in one portion. After 30 minutes at 20° C., the solution was poured into a separatory funnel containing 12 mL water and 600 mg sodium sulfite. The mixture was then shaken and extracted with ethyl acetate. The combined extracts were dried (MgSO$_4$), filtered, and evaporated to afford 600 mg solid. Flash chromatography through a column of silica gel eluting with 2:1 hexane:ethyl acetate, then acetone afforded 250 mg of starting material and 230 mg of aldehyde VI, characterized by its NMR spectrum.

PREPARATION N.

Transketalization of Aldehyde VI to Aldehydes VIIA and VIIB (Scheme 1) and 2R,3R,4S-2,4-dimethyl-3-hydroxyhexanoic acid To a solution of 8 g of pyridinium tosylate in 80 mL of dry methanol was added 16.3 g of aldehyde VI from Preparation M. The mixture was stirred at 20° C. for 1.5 hours before 4 mL triethylamine was added. The mixture was then transferred to a separatory funnel containing 4.4 g sodium bicarbonate and 500 mL water. The mixture was extracted with ether and the aqueous layer was then acidified with 2N HCl and extracted with ethyl acetate to recover 1.4 g of 2R,3R,4S-2,4-dimethyl-3-hydroxyhexanoic acid as an amber oil. The ether extracts were combined and dried over magnesium sulfate. Filtration and evaporation of the solvent afforded 15.5 g solid as 1:1:1 mixture of methoxy ketals VIIA and VIIB and aldehyde-acid VI, in addition to some minor products with a slower Rf than VIIB but faster than VI (isomer VIIB which has lost some silyl groups). The mixture was separated by flash column chromatography on 550 g of silica gel eluted with 3:1 and then 2:1 hexane:ethyl acetate to yield 5.1 g VIIA, 4.0 g VIIB, and 3.9 g VI, each characterized by NMR and mass spectroscopy. The stereochemical assignment at C21 for isomers VIIA and VIIB was based on the nonreversible conversion of VIIA to VIIB when each pure isomer was resubjected to acidic methanol. Isomer VIIB being the thermodynamically stable isomer has been assigned the axial methoxyl/equitorial formyl configuration. The chiral acid was esterified with excess diazomethane and purified by flash chromatography with 15% ethyl acetate-hexane to yield 1 g of methyl ester $[^-]_D = -9.5°$, c=8.9 g/dL dichloromethane, characterized by its NMR spectrum.

PREPARATION O.

(S)-3-Iodo-1-phenyl-1-propanol.

Commerically available (S)-3-chloro-1-phenyl-1-propanol (6 g) was heated with excess sodium iodide (4 equiv., 18 g) and a few drops of triethylamine in 30 mL of methyl ethyl ketone at 100° C. for 20 hours. A sample was taken and monitored by NMR to determine the extent of conversion. The solvent was removed in vacuo and the residue was taken up in dichloromethane and filtered to remove the salts and the iodoalcohol was purified by flash chromatography to yield 6.9 g of product.

PREPARATION P.

(S)-3-Iodo-1-phenyl-1-trimethylsilyloxypropane.

The iodoalcohol obtained in Preparation O, was protected as the trimethylsilylether with either BSTFA in DMF or trimethylsilyltriflate and triethylamine in dichloromethane following standard procedures. For example, to 800 mg of iodoalcohol in 4 mL of dichloromethane was added 2 mL of triethylamine and 1.5 mL of trimethylsilyltriflate. After 30 minutes the solvent was removed in vacuo and the residue was flash chromatographed to afford 990 mg of product characterized by its NMR and mass spectra.

PREPARATION Q.

(S)-[3-Phenyl-3-trimethylsilyloxy)propyl]phosphonium iodide.

A solution of 408 mg of iodophenylpropyltrimethylsilyl ether and 321 mg (1 equiv.) of triphenylphosphine in 5 mL of toluene and a drop of triethylamine was heated under nitrogen at 100° C. for 64 hours. The toluene was removed in vacuo and the residue was triturated in ether-hexane to afford 500 mg of solid product characterized by its NMR and mass spectra.

PREPARATION R.

General procedure for the preparation of 3-Chloro-1-alkyl(aryl)-1-propanol.

3-Chloropropanal prepared by addition of dry hydrogen chloride to distilled acrolein (Shriner et al., J. Org. Chem. 103–105, (1939)) is added to an excess of the appropriate Grignard reagent at 20° C. After 30 minutes the mixture is cooled with an acetone-dry ice bath and quenched with an aqueous ammonium chloride solution. The product is isolated by ether extraction and purified by silica gel chromatography.

PREPARATION S.

[(3-Alkyl(aryl)-3-trimethylsilyloxy)propyl]triphenylphosphonium iodide.

The corresponding 3-chloro-1-alkyl(aryl)-1-propanol obtained in Preparation R is converted to the iodoalcohol by the procedure described in Preparation O and then protected as the trimethylsilylether as in Preparation P. The corresponding phosphonium salt was prepared as outlined in Preparation Q. Following that protocol the following salts have been prepared and characterized:

(R,S)-[(3-cyclopentyl-3-trimethylsilyloxy)propyl]triphenylphosphonium iodide,
(R,S)-[(3-cyclohexyl-3-trimethylsilyloxy)propyl]triphenylphosphonium iodide,
[(3-(2-butyl)-3-trimethylsiloxy)propyl]triphenylphosphonium iodide (diastereomeric mixture).

Starting with the appropriate 3-chloro-1-alkyl(aryl)-1-propanol following the procedure for the above cases, the following salts are obtained:

(R,S)-[(3-benzyl)-3-trimethylsilyloxy)propyl]triphenylphosphonium iodide;
(R,S)-[3-(3-furyl)-3-trimethylsilyloxy)propyl]triphenylphosphonium iodide;
(R,S)-[3-(2-thienyl)-3-trimethylsilyloxy)propyl]triphenylphosphonium iodide;
(R,S)-[(3-(4-pyridyl)-3-trimethylsilyloxy)propyl]triphenylphosphonium iodide;
(R,S)-[(3-(1-octyl)-3-trimethylsilyloxy)propyl]triphenylphosphonium iodide;
(R,S)-[(3-(1-ethyl)-3-trimethylsiloxy)propyl]triphenylphosphonium iodide.

PREPARATION T.

24-Desmethyl-25-des-(2-butyl)-25-phenyl-avermectin B1.

A Wittig condensation of the yield derived from (S)-[(3-phenyl-3-trimethylsilyloxy)propyl]triphenylphosphonium iodide (130 mg) of Preparation Q with aldehyde VIIB gave the cis-olefin precursor (74 mg) which was cyclized to the spiroketal (90%) with PPTS and methanol. Removal of the silyl protecting groups with HF-pyridine-THF gave the title product (50%) characterized by its NMR and mass spectra.

PREPARATION U.

24-Desmethyl-25-des-(2-butyl)-25-cyclopentyl-avermectin B1 and
24-Desmethyl-25-des-(2-butyl)-25-epi-cyclopentyl-avermectin B1.

A Wittig condensation of 183 mg of (R,S)-[(3-cyclopentyl-3-trimethylsilyloxy)propyl]triphenylphosphonium iodide from Preparation S with 300 mg of aldehyde VIIB gave 283 mg of olefinic adduct. Cyclization of 153 mg of this adduct gave 52 mg of the normal C25 isomer and 61 mg of the epi-C25 isomer (separated by TLC). Each isomer was deprotected with HF-pyridine-THF to afford 21 mg of the title compound characterized by its NMR and mass spectra.

PREPARATION V.

24-Desmethyl-25-des-(2-butyl)-25-cyclohexyl-avermectin B1a and 24-Desmethyl-25-des-(2-butyl)-25-epi-cyclohexyl-avermectin B1a.

The Wittig reaction from 204 mg of (R,S)-[(3-cyclohexyl-3-trimethylsilyloxy)propyl]triphenylphosphonium iodide and 297 mg of aldehyde VIIA gave 130 mg of adduct. Cyclization of 116 mg of the adduct gave 35 mg of C25-normal and 40 mg of slower eluting C25-epi product (from TLC in 15% ethyl acetate-hexane). Desilylation of the individual compounds gave 13 mg of the normal C25 product, characterized by its NMR and mass spectra.

PREPARATION W.

Preparation of 3-Chloro-2-ethyl-1-alkyl(aryl)-1-propanols and 3-chloro-2-methyl-1-alkyl(aryl)-1-propanols.

2-Ethylacrolein (39 g) was chilled to 0° C. in a flask and dry HCl gas was bubbled in until 17 g (1 equiv.) was absorbed. The mixture was then immediately distilled at reduced pressure to afford 9.7 g of 2-ethyl-3-chloropropanal (b.p. 47° C./14 torr). This was added to an excess of the appropriate Grignard reagent in ether at room temperature as described in Preparation R or to an alkyl(aryl) lithium at −78° C. to produce the corresponding 3-chloro-2-ethyl-1-alkyl(aryl)-1-propanol:
3-chloro-2-ethyl-1-phenyl-1-propanol;
3-chloro-2-ethyl-1-cyclopentyl-1-propanol;
3-chloro-2-ethyl-1-(3,5-dichlorophenyl)-1-propanol.
Additionally, reduction of the 2-ethyl-3-chloropropanal with sodium borohydride in methanol provides the 2-ethyl-3-chloro-1-propanol.

In similar fashion the hydrochlorination of 2-methylacrolein and subsequent reaction with a Grignard reagent or alkyl(aryl) lithium produce the 3-chloro-2-methyl-1-alkyl(aryl)-1-propanols:
3-chloro-2-methyl-1-(4-methoxyphenyl)-1-propanol;
3-chloro-2-methyl-1-(3,5-dichlorophenyl)-1-propanol;
3-chloro-2-methyl-1-(4-acetylaminophenyl)-1-propanol;
3-chloro-2-methyl-1-benzyl-1-propanol;
3-chloro-2-methyl-1-phenyl-1-propanol.

PREPARATION X.

[(2-Ethyl-3-alkyl(aryl)-3-trimethylsilyloxy)propyl]-triphenylphosphonium iodide and [(2-Methyl-3-alkyl(aryl)-3-trimethylsilyloxy)propyl]triphenylphosphonium iodide.

Following the process give in Preparations O, P and Q, the chloropropanols described in Preparation W are converted to their corresponding phosphonium iodides:
[(2-methyl-3-(4-methoxyphenyl)-3-trimethylsilyloxy)propyl]triphenylphosphonium iodide;
[(2-methyl-3-(3,5-dichlorophenyl)-3-trimethylsilyloxy)propyl]triphenylphosphonium iodide;
[(2-methyl-3-(4-acetylaminophenyl)-3-trimethylsilyloxy)propyl]triphenylphosphonium iodide;
[(2-methyl-3-benzyl-3-trimethylsilyloxy)propyl]triphenylphosphonium iodide;
[(2-methyl-3-phenyl-3-trimethylsilyloxy)propyl]triphenylphosphonium iodide;
[(2-ethyl-3-(4-methoxyphenyl)-3-trimethylsilyloxy)propyl]triphenylphosphonium iodide;
[(2-ethyl-3-phenyl-3-trimethylsilyloxy)propyl]triphenylphosphonium iodide;
[(2-ethyl-3-(3,5-dichlorophenyl)-trimethylsilyloxy)propyl]triphenylphosphonium iodide;
[(2-ethyl-3-benzyl-3-trimethylsilyloxy)propyl]triphenylphosphonium iodide;
[(2-ethyl-3-trimethylsilyloxy)propyl]triphenylphosphonium iodide;

PREPARATION Y.

(S)- and (R)-[(3-trimethylsilyloxy)butyl]triphenylphosphonium iodide.

Commercially available (S)-1,3-butanediol, 1.47 g, was dissolved in 10 mL dichloromethane and 5 mL triethylamine. To this was added 3.22 g p-toluenesulfonyl chloride. After 1.5 hours the primary monotosylate was purified by silica gel flash chromatography to afford 2.85 g of (S)-3-hydroxybutyl-1-p-tosylate. This was converted to 2.33 g of (S)-1-iodo-3-hydroxybutane by refluxing with 4.2 g of sodium iodide in 20 mL of acetone and 5 drops of triethylamine (17 hours). The resulting iodoalcohol was silylated with bis(trimethylsilyl)trifluoroacetamide in dimethylformamide at room temperature. The corresponding (S)-[(3-trimethylsilyloxy)butyl]triphenylphosphonium iodide was prepared by heating the iodosilylether with an equivalent of triphenylphosphine in toluene 48 hours at 100° C. Starting with the commercially available (R)-1,3-butanediol, the corresponding (R)-[(3-trimethylsilyloxy)butyl]triphenylphosphonium iodide is prepared and characterized by NMR and mass spectra.

PREPARATION Z.

[(2-Methyl-3-trimethylsilyloxy)butyl]triphenylphosphonium iodide.

Commercially available 4-hydroxy-3-methyl-2-butanone, 10.4 g, (technical grade 65%) was reduced with excess lithium aluminum hydride (25 mL of a 1.0M solution) in 50 mL ether and worked up with the addition of 2 mL ethyl acetate, 1 mL water, 1 mL 15% sodium hydroxide, and anhydrous sodium sulfate. The solid was extracted overnight in a Sohxlet extractor with 250 mL refluxing ether. The ether was removed in vacuo and the diol was distilled in a Kugelrohr at 150° C., 12 torr to give 3.89 g of product. This 1,3-dihydroxy-2-methylbutane (as a mixture of diastereomers) was converted to the promary tosylate was in Preparation Y and then to the iodoalcohol with sodium iodide. Subsequent silylation with bis(trimethylsilyl)trifluoroacetamide and treatment with triphenylphosphine in toluene gave the title phosphonium iodide (diastereoisomers) characterized by its NMR and mass spectra.

PREPARATION AA.

[(2-Methyl-3-trimethylsilyloxy)pentyl]triphenylphosphonium iodide.

Commercially available 1-hydroxy-2-methyl-3-butene (1.91 g) was silylated with 5 g t-butyldimethylsilyl chloride and 4.7 g imidazole in 5 mL DMF and 5 mL dichloromethane for 3 hours. The mixture was poured into water and extracted with 9:1 hexane:ether. The extracts were combined and concentrated to afford 4.3 g 1-t-butyldimethylsilyloxy-2-methyl-3-butene which was used without further purification. The silyloxybutene and 3 mg Sudan 7B red dye were dissolved in 50 mL dichloromethane and treated at −78° C. with ozone until the red color was discharged. The solution was then warmed to room temperature for 30 minutes before cooling back to −78° C. A solution of 2.0M ethyl magnesium bromide (30 mL) in THF was added over 10 minutes and the resulting mixture was warmed to room temperature for 45 minutes before cautious addition of aqueous ammonium chloride at low temperature to quench the excess Grignard reagent. Extraction of the mixture with ether and evaporation of the solvent yielded 3.96 g residual oil confirmed by NMR to be the desired product. This was dissolved in 20 mL of methanol with 475 mg of p-toluenesulfonic acid monohydrate and stirred at 20° C. for 2 hours. The methanol was then removed in vacuo and the residual product was flash chromatographed on 400 g of silica gel (1:1 hexane:ethyl acetate) to yield 1.1 g of 1,3-dihydroxy-2-methyl-pentane as a diastereomeric mixture (by NMR). Subsequent conversion to the title phosphonium iodide was accomplished following the procedure set forth in Preparations Y and Z.

PREPARATION BB.

25-Des-(2-butyl)-25-alkyl(aryl)-avermectin B1a and 25-Des-(2-butyl)-25-epialkyl(aryl)-avermectin B1a The Wittig condensations of [(2-methyl-3-(4-methoxyphenyl)-3-trimethylsilyloxy)propyl]triphenylphosphonium iodide; [(2-methyl-3-(3,5-dichlorophenyl)-3-trimethylsilyloxy)propyl]triphenylphosphonium iodide; [(2-methyl-3(4-acetylaminophenyl-3-trimethylsilyloxy)-propyl]triphenylphosphonium iodide; [(2-methyl-3-benzyl-3-trimethylsilyloxy)propyl]triphenylphosphonium iodide; and [(2-methyl-3-phenyl-3-trimethylsilyloxy)-propyl]triphenylphosphonium iodide (Preparation X); [(2-methyl-3-trimethylsilyloxy)butyl]triphenylphosphonium iodide (Preparation Z); and [(2-methyl-3-trimethylsilyloxy)pentyl]triphenylphosphonium iodide (Preparation AA) with either aldehyde VIIA or VIIB and subsequent cyclization and desilylation provide respectively:

25-des-(2-butyl)-25-(4-methoxyphenyl)-avermectin B1a;
25-des-(2-butyl)-25-(3,5-dichlorophenyl)-avermectin B1a;
25-des-(2-butyl)-25-(4-acetylaminophenyl)-avermectin B1a;
25-des-(2-butyl)-25-benzyl-avermectin B1a;
25-des-(2-butyl)-25-phenyl-avermectin B1a;
25-des-(2-butyl)-25-methyl-avermectin B1a;
25-des-(2-butyl)-25-ethyl-avermectin B1a and their corresponding C25-epimers, which are characterized by their NMR and mass spectra.

PREPARATION CC.

24-Desmethyl-25-des-(2-butyl)-25-heterocyclo-avermectin B1a and
24-Desmethyl-25-des-(2-butyl)-25-epi-heterocyclo-avermectin B1a The Wittig condensations of (R,S,)-[3-(3-furyl)-3-trimethylsilyloxy)propyl]triphenylphosphonium iodide;
(R,S,)-[3-(2-thienyl)-3-trimethylsilyloxy)propyl]triphenylphosphonium iodide; and
(R,S,)-[3-(4-pyridyl)-3-trimethylsilyloxy)propyl]triphenylphosphonium iodide; (obtained following the procedures of Preparation S) with either aldehyde VIIA or VIIB and subsequent cyclization and desilylation provide respectively:

24-desmethyl-25-des-(2-butyl)-25-(3-furyl)-avermectin B1a;
24-desmethyl-25-des-(2-butyl)-25-(2-thienyl)-avermectin B1a;
24-desmethyl-25-des-(2-butyl)-25-(4-pyridyl)-avermectin B1a;
and their corresponding 25-epimers, which are characterized by their NMR and mass spectra.

What is claimed is:

1. A compound having the formula:

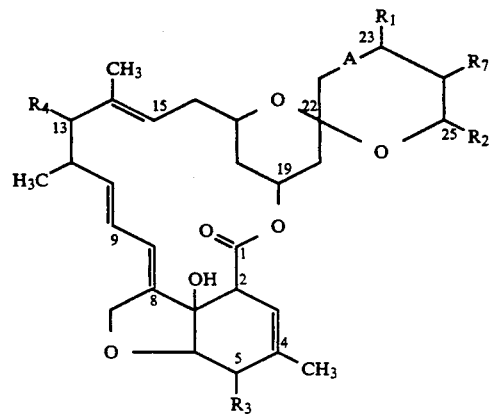

wherein:
A at the 22,23 position represents
  (1) a single bond and wherein $R_1$ is
    (a) hydrogen,
    (b) hydroxy, or
    (c) oxo; or
  (2) a double bond and $R_1$ is absent;
$R_2$ is
  (1) $C_{1-4}$ alkyl,
  (2) substituted $C_{1-4}$ alkyl with 1 to 3 substituents selected from $C_{4-6}$ cycloalkyl, phenyl, and halo,
  (3) alpha-branched $C_{3-8}$ alkyl,
  (4) $C_{2-8}$ alkenyl,
  (5) $C_{2-6}$ alkynyl,
  (6) $C_{1-6}$ alkoxy $C_{1-6}$ alkyl,
  (7) $C_{1-6}$ alkylthio $C_{1-6}$ alkyl,
  (8) $C_{4-6}$ cycloalkyl or $C_{4-6}$ cycloalkenyl, either unsubstituted or substituted with 1 to 3 substitutents selected from
    (a) methylene,
    (b) halo, and
    (c) $C_{1-4}$ alkyl,
  (9) 3 to 6 membered nitrogen, oxygen or sulfur containing heterocycle containing one heteroatom saturated or unsaturated, connected through a carbon atom on the heterocycle to C-25 either unsubstituted or substituted with 1 to 3 substitutents selected from
    (a) $C_{1-4}$ alkyl, and
    (b) halo, or
  (10) phenyl, either substituted or unsubstituted with 1 to 3 substitutents selected from
    (a) $C_{1-3}$ alkyl, and
    (b) halo;
$R_3$ is
  (1) hydroxy,
  (2) $C_{1-6}$ alkoxy,
  (3) $C_{2-6}$ alkanoyloxy,
  (4) oxo, or (5) oximino;
$R_7$ is hydrogen or $C_{1-6}$ alkyl, either straight chain or branched; and
$R_4$ is

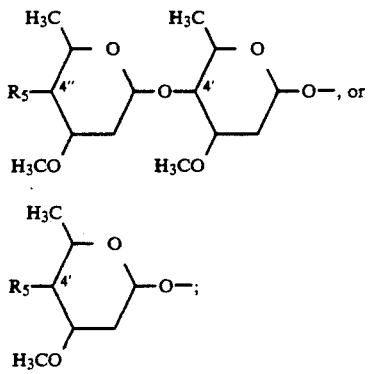

wherein:
$R_5$ is
(1) $S(O)_nR_6$ wherein n is 0, 1 or 2, or
(2) $SCOR_6$
wherein:
$R_6$ is
(1) hydrogen,
(2) $C_{1-8}$ alkyl either straight or branched chain and either unsubstituted or substituted with 1-3 substitutents selected from
(a) halo,
(b) hydroxy,
(c) $C_{1-3}$ alkoxy,
(d) phenoxy,
(e) $C_{1-3}$ alkylthio,
(f) $C_{1-3}$ alkylsulfinyl,
(g) $C_{1-3}$ alkylsulfonyl,
(h) amino,
(i) $C_{2-6}$ alkanoylamino,
(j) $C_{1-3}$ alkylamino,
(k) di($C_{1-3}$ alkyl)amino,
(l) halo $C_{1-3}$ alkoxycarbonylamino,
(m) oxo,
(n) carboxy, and
(o) $C_{1-3}$ alkoxycarbonyl,
(3) $C_{2-8}$ alkanoyl either unsubstituted or substituted with 1-3 substituents selected from
(a) halo,
(b) hydroxy,
(c) $C_{1-3}$ alkoxy,
(d) phenoxy,
(e) $C_{1-3}$ alkylthio,
(f) $C_{1-3}$ alkylsulfinyl,
(g) $C_{1-3}$ alkylsulfonyl,
(h) amino,
(i) $C_{2-6}$ alkanoylamino,
(j) $C_{1-3}$ alkylamino,
(k) di($C_{1-3}$ alkyl)amino,
(l) halo $C_{1-3}$ alkoxycarbonylamino,
(m) oxo,
(n) carboxy, and
(o) $C_{1-3}$ alkoxycarbonyl,
(4) $C_{3-8}$ cycloalkyl either unsubstituted or substituted with 1-3 substituents selected from
(a) halo,
(b) $C_{1-3}$ alkoxy,
(c) sulfonamido, (d) amino,
(e) $C_{1-3}$ alkylamino,
(f) di($C_{1-3}$ alkyl)amino, and
(g) $C_{2-6}$ alkanoylamino.

2. The compound of claim 1, wherein:
A at the 22,23 position represents
(1) a single bond and wherein $R_1$ is
(a) hydrogen, or
(b) hydroxy, or
(2) a double bond and $R_1$ is absent;
$R_2$ is
(1) alpha-branched $C_3-C_8$ alkyl,
(2) alpha-branched $C_3-C_8$ alkenyl,
(3) $C_{4-6}$ cycloalkyl,
(4) $C_{4-6}$ cycloalkenyl,
(5) phenyl, or
(6) p-fluoro-phenyl;
$R_3$ is
(1) hydroxy, or
(2) oximino;
$R_7$ is methyl; and
$R_4$ is

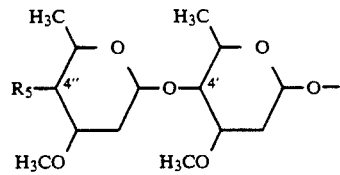

wherein
$R_5$ is
(1) $S(O)_nR_6$ wherein n is 0, 1 or 2, or
(2) $SCOR_6$;
wherein:
$R_6$ is
(1) hydrogen,
(2) $C_{1-4}$ alkyl either straight or branched chain and either unsubstituted or substituted with 1-3 substitutents selected from
(a) halo,
(b) hydroxy,
(c) $C_{1-3}$ alkoxy,
(d) $C_{1-3}$ alkylthio,
(e) $C_{1-3}$ alkylsulfonyl,
(f) amino,
(g) $C_{2-3}$ alkanoylamino,
(h) $C_{1-3}$ alkylamino,
(i) di($C_{1-3}$ alkyl)amino,
(j) carboxy, and
(k) $C_{1-3}$ alkoxycarbonyl, or
(3) $C_{2-5}$ alkanoyl either unsubstituted or substituted with 1-3 substituents selected from
(a) halo,
(b) hydroxy,
(c) $C_{1-3}$ alkoxy,
(d) $C_{1-3}$ alkylthio,
(e) $C_{1-3}$ alkylsulfinyl,
(f) $C_{1-3}$ alkylsulfonyl,
(g) amino,
(h) $C_{1-3}$ alkylamino,
(i) di($C_{1-3}$ alkyl)amino.

3. The compound of claim 1, wherein:
A at the 22,23 position represents
(1) a single bond and wherein $R_1$ is
(a) hydrogen, or
(b) hydroxy, or (2) a double bond and $R_1$ is absent;
$R_2$ is
(1) 2-propyl,
(2) 2-butyl,
(3) 2-buten-2-yl,
(4) 2-penten-2-yl,
(5) 4-methyl-2-penten-2-yl,
(6) cyclopentyl,
(7) cyclopentenyl,
(8) cyclohexyl,
(9) cyclohexenyl,
(10) phenyl, or
(11) p-fluoro-phenyl;
$R_3$ is
(1) hydroxy, or
(2) oximino;
$R_7$ is methyl; and
$R_4$ is

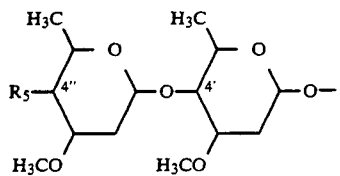

wherein
$R_5$ is
(1) $S(O)_nR_6$ wherein n is 0, 1, 2 or
(2) $SCOR_6$;
wherein
$R_6$ is $C_{1-3}$ alkyl either straight or branched chain and either unsubstituted or substituted with 1-3 substitutents selected from
(1) hydroxy,
(2) $C_{1-2}$ alkoxy,
(3) amino,
(4) acetylamino,
(5) $C_{1-2}$ alkylamino,
(6) dimethylamino, and
(7) halo.

4. The compound of claim 1 which is:
(a) 4''-deoxy-4''-epi-methylthio-avermectin B1a/B1b,
(b) 4''-deoxy-22,23-dihydro-4''-epi-methylthio-avermectin B1a/B1b,
(c) 4''-deoxy-4''-epi-methylsulfinyl-avermectin B1a/B1b,
(d) 4''-deoxy-4''-epi-methylsulfonyl-avermectin B1a/B1b,
(e) 4''-deoxy-4''-methylthio-avermectin B1a/B1b,
(f) 4''-deoxy-22,23-dihydro-4''-methylthio-avermectin B1a/B1b,
(g) 4''-deoxy-4''-methylsulfinyl-avermectin B1a/B1b,
(h) 4''-deoxy-4''-methylsulfonyl-avermectin B1a/B1b,
(i) 4''-deoxy-5-oximino-4''-epi-methylthio-avermectin B1a/B1b,
(j) 4''-deoxy-22,23-dihydro-5-oximino-4''-epi-methylthio-avermectin B1a/B1b,
(k) 4''-deoxy-5-oximino-4''-epi-methylsulfinyl-avermectin B1a/B1b,
(l) 4''-deoxy-5-oximino-4''-epi-methylsulfonyl-avermectin B1a/B1b,
(m) 4''-deoxy-5-oximino-4''-methylthio-avermectin B1a/B1b,
(n) 4''-deoxy-22,23-dihydro-5-oximino-4''-methylthio-avermectin B1a/B1b,
(o) 4''-deoxy-5-oximino-4''-methylsulfinyl-avermectin B1a/B1b,
(p) 4''-deoxy-5-oximino-4''-methylsulfonyl-avermectin B1a/B1b,
(q) 4''-deoxy-4''-(2-hydroxyethyl)thio-avermectin B1a/B1b,
(r) 4''-deoxy-4''-epi-(2-hydroxyethyl)thio-avermectin B1a/B1b,
(s) 4''-deoxy-5-oximino-4''-(2-hydroxyethyl)thio-avermectin B1a/B1b,
(t) 4''-deoxy-5-oximino-4''-(2-hydroxyethyl)-thio-avermectin B1a/B1b,
(u) 4''-deoxy-22,23-dihydro-4''-(2-hydroxyethyl)-thio-avermectin B1a/B1b,
(v) 4''-deoxy-22,23-dihydro-5-oximino-4''-(2-hydroxyethyl)thio-avermectin B1a/B1b,
(w) 4''-deoxy-22,23-dihydro-5-oximino-4''-epi-(2-hydroxyethyl)thio-avermectin B1a/B1b,
(x) 4''-deoxy-4''-(2-hydroxyethyl)sulfinyl-avermectin B1a/B1b,
(y) 4''-deoxy-4''-epi-(2-hydroxyethyl)sulfinyl-avermectin B1a/B1b,
(z) 4''-deoxy-5-oximino-4''-(2-hydroxyethyl)sulfinyl-avermectin B1a/B1b,
(aa) 4''-deoxy-5-oximino-4''-epi-(2-hydroxyethyl)sulfinyl-avermectin B1a/B1b,
(bb) 4''-deoxy-22,23-dihydro-4''-(2-hydroxyethyl)sulfinyl-avermectin B1a/B1b,
(cc) 4''-deoxy-22,23-dihydro-4''-epi-(2-hydroxyethyl)-sulfinyl-avermectin B1a/B1b,
(dd) 4''deoxy-22,23-dihydro-5-oximino-4''-(2-hydroxyethyl)sulfinyl-avermectin B1a/B1b,
(ee) 4''-deoxy-22,23-dihydro-5-oximino-4''-epi-(2-hydroxyethyl)sulfinyl-avermectin B1a/B1b,
(ff) 4''-deoxy-4''-(2-hydroxyethyl)sulfonyl-avermectin B1a/B1b,
(gg) 4''-deoxy-4''-epi-(2-hydroxyethyl)sulfonyl-avermectin B1a/B1b,
(hh) 4''-deoxy-5-oximino-4''-(2-hydroxyethyl)sulfonyl-avermectin B1a/B1b,
(ii) 4''-deoxy-5-oximino-4''-epi-(2-hydroxyethyl)sulfonyl-avermectin B1a/B1b,
(jj) 4''-deoxy-22,23-dihydro-4''-(2-hydroxyethyl)sulfonyl-avermectin B1a/B1b,
(kk) 4''-deoxy-22,23-dihydro-4''-epi-(2-hydroxyethyl)-sulfonyl-avermectin B1a/B1b,
(ll) 4''-deoxy-22,23-dihydro-5-oximino-4''-(2-hydroxyethyl)-sulfonyl-avermectin B1a/B1b,
(mm) 4''-deoxy-22,23-dihydro-5-oximino-4''-epi-(2-hydroxyethyl)-sulfonyl-avermectin B1a/B1b,
(nn) 4''-deoxy-4''-epi-methylthio-25-des-(2-butyl)-25-cyclohexyl-avermectin,
(oo) 4''-deoxy-4''-epi-methylthio-25-des-(2-butyl)-25-phenyl-avermectin,
(pp) 4''-deoxy-4''-epi-methylthio-25-des-(2-butyl)-25-[2-(4-methylpenten-2-yl)]-avermectin,
(qq) 4''-deoxy-4''-epi-(2-amino)ethylthio-25-des-(2-butyl)-25-cyclohexen-2-yl-avermectin,
(rr) 4''-deoxy-4''-epi-trifluoromethylthio-avermectin B1a/B1b, and
(ss) 4''-deoxy-4''-epi-2,2,2-trifluoroethylthio-avermectin B1a/B1b, 5. A protected derivative of a compound of claim 1 wherein $R_3$ is tert.-butyldimethylsilyloxy.

6. The compound of claim 5 which is
(a) 4''-deoxy-4''-trifluoromethanesulfonyl-5-O-tert.-butyldimethylsilyl-avermectin B1a/B1b.

7. A method for the therapeutic treatment of parasitic infections of animals or plants, which comprises topical, oral or parenteral treatment of the animal or topical treatment of the plant or the soil in which the plant grows with an effective amount of a compound of claim 1.

8. A composition useful for the therapeutic antiparasitic treatment of animals or plants which comprises an inert carrier and a compound of claim 1.

* * * * *